(12) United States Patent
Wang et al.

(10) Patent No.: US 11,547,674 B2
(45) Date of Patent: Jan. 10, 2023

(54) PROTEIN-POLYMER HYBRID BIOMATERIALS

(71) Applicant: The Regents of the University of California, Oakland, CA (US)

(72) Inventors: Szu-Wen Wang, Irvine, CA (US); Tae Il Kim, Irvine, CA (US); Kenneth J. Shea, Irvine, CA (US); Krista Fruehauf, Irvine, CA (US); Edward L. Nelson, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 597 days.

(21) Appl. No.: 16/519,690

(22) Filed: Jul. 23, 2019

(65) Prior Publication Data

US 2020/0054574 A1 Feb. 20, 2020

Related U.S. Application Data

(60) Provisional application No. 62/730,453, filed on Sep. 12, 2018, provisional application No. 62/718,710, filed on Aug. 14, 2018.

(51) Int. Cl.
*A61K 9/51* (2006.01)

(52) U.S. Cl.
CPC .......... *A61K 9/5138* (2013.01); *A61K 9/5169* (2013.01)

(58) Field of Classification Search
None
See application file for complete search history.

(56) References Cited

U.S. PATENT DOCUMENTS 8,075,916 B2 * 12/2011 Song ................ C08G 65/33306
514/8.5
9,539,245 B2 1/2017 Peters

OTHER PUBLICATIONS

Thornton et al.,"Enzyme-responsive hydrogel particles for the controlled release of proteins: designing peptide actuators to match payload", Soft Matter 4: 821-827 (Year: 2008).*
Fruehauf et al. "Biomaterials responsive to metabolites of disease." Abstracts of Papers of the American Chemical Society. vol. 256. 1155 16th St, NW, Washington, DC 20036 USA: Amer Chemical Soc, 2018.
Kim et al. Engineering Drug Delivery Materials Responsive to Disease Metabolites. Biomedical Engineering Society (BMES) Annual Meeting, Oct. 17-20, 2018 Atlanta, Georgia. Abstract.
Molino et al. Display of DNA on Nanoparticles for Targeting Antigen Presenting Cells. ACS Biomater Sci Eng. Apr. 10, 2017; 3(4): 496-501. doi:10.1021/acsbiomaterials.7b00148.
Molino et al. Viral-mimicking protein nanoparticle vaccine for eliciting antitumor responses. Biomaterials. Apr. 2016 ; 86: 83-91. doi:10.1016/j.biomaterials.2016.01.056.
Neek et al. Co-delivery of human cancer-testis antigens with adjuvant in protein nanoparticles induces higher cell-mediated immune responses. Biomaterials 156 (2018) 194-203.
Wang. Nanoparticle-Modulated Response Against Tumor-Associated Antigens. NIH website, Sep. 2014, Abstract.
Kokufata et al. "Saccharide-sensitive phase transition of a lectin-loaded gel." Nature 351.6324 (1991): 302.
Miyata et al. "Preparation of poly (2-glucosyloxyethyl methacrylate)-concanavalin A complex hydrogel and its glucose-sensitivity." Macromolecular Chemistry and Physics197.3 (1996): 1135-1146.
Miyata et al. "Preparation of reversibly glucose-responsive hydrogels by covalent immobilization of lectin in polymer networks having pendant glucose." Journal of Biomaterials Science, Polymer Edition 15.9 (2004): 1085-1098.
Molino et al. "Biomimetic protein nanoparticles facilitate enhanced dendritic cell activation and cross-presentation." ACS nano 7.11 (2013): 9743-9752.
Swart et al. "Combination approaches with immune-checkpoint blockade in cancer therapy." Frontiers in oncology 6 (2016): 233.

* cited by examiner

*Primary Examiner* — Anand U Desai
(74) *Attorney, Agent, or Firm* — Nguyen Tarbet LLC

(57) ABSTRACT

For applications in drug delivery, "smart" materials have been designed to respond to conditions within microenvironments of tissues or cells. The present invention features stimuli-responsive cross-linked hydrogels that respond to specific metabolites of disease. For example, protein-polymer materials of the present invention are configured to release their drug cargo upon encountering the higher lactate concentrations within tumor microenvironments.

3 Claims, 12 Drawing Sheets

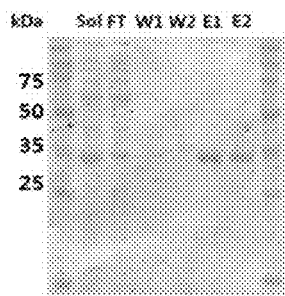 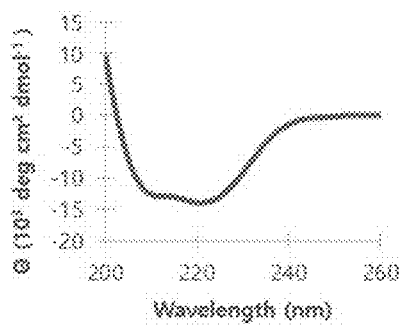 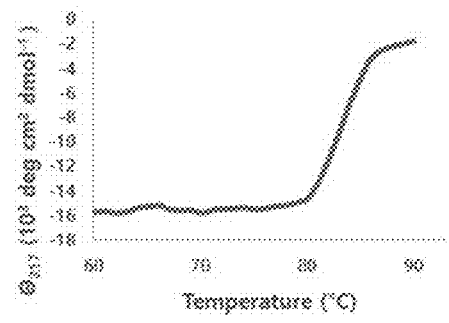
FIG. 9A     FIG. 9B     FIG. 9C
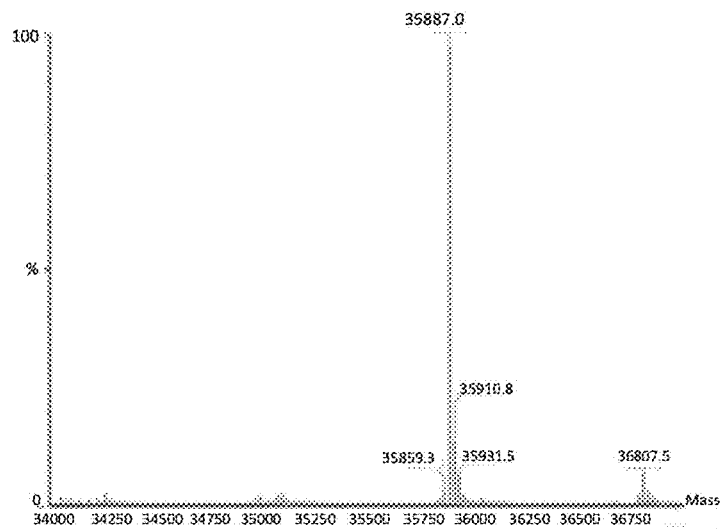
FIG. 9D
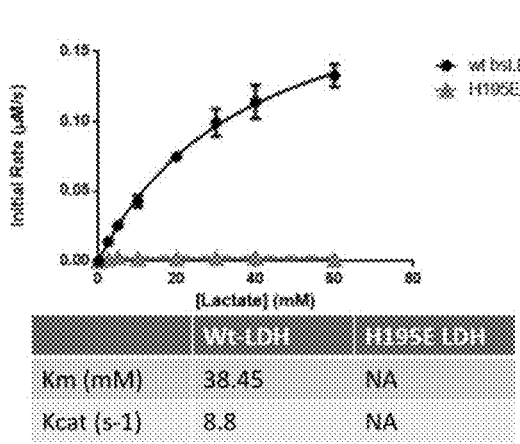 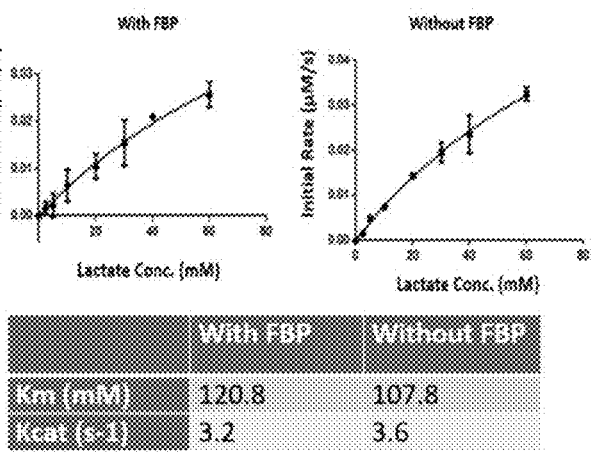
FIG. 10A     FIG. 10B

PROTEIN-POLYMER HYBRID BIOMATERIALS

CROSS-REFERENCES TO RELATED APPLICATIONS

This application is a non-provisional application and claims benefit of U.S. Provisional Patent Application No. 62/718,710, filed Aug. 14, 2018, and U.S. Provisional Patent Application No. 62/730,453, filed Sep. 12, 2018, the specifications of which are incorporated herein in their entirety by reference.

FIELD OF THE INVENTION

The present invention relates to biomaterials for drug delivery. More specifically, the present invention relates to protein-polymer hybrid biomaterials that are responsive to metabolites of disease.

BACKGROUND OF THE INVENTION

Smart polymers are materials that respond to certain external stimuli. Stimuli responsive polymers are an efficient means of targeted therapy. Compared to conventional agents, they increase bioavailability and efficacy. In particular, polymer hydrogel nanoparticles (NPs) can be designed to selectively release their payload when exposed to a specific environment. The behavior of "smart" stimuli-responsive biomaterials is triggered by environmental conditions. In cancer therapy, polymers for drug delivery have typically been designed to respond to environmental conditions such as low pH (pH~6-7 in the tumor extracellular microenvironment or pH~5.5 in intracellular endosomes), slightly hyperthermic conditions in tumor tissues (only 1-2° C. above healthy tissues), or proteases. These biomaterials generally show benefit over traditional materials, but adequate in vivo therapeutic responses can sometimes be difficult to consistently achieve, partially because the differences between healthy and diseased environments are often not sufficiently large or unique. Alternative triggers, such as ultrasound, light, and magnetic force, require application of external conditions that may also be difficult to implement in internal tumor or tissues.

Cancerous tissues have a high lactic acid concentration, leading to a lower pH than normal, which can trigger NPs to release payloads. In 1924, Otto Warburg first observed that cancer cells metabolize glucose differently than normal cells, independent of whether oxygen was present (aerobic) or not (anaerobic) in the local environment, and these changes resulted in an accumulation of lactate in tumors. The Warburg effect is a result of an alternative metabolic pathway utilized by cancer cells and is now considered to be a hallmark of cancer. The vast majority of tumors accumulate lactate in its local environment through a metabolic shift from "normal" oxidative phosphorylation (via the TCA cycle) to aerobic glycolysis (with lactate production also being possible in tumors via the less-common anaerobic glycolysis). This shift to the glycolysis pathway, which produces lactate, is extensive and observed in the majority of different types of cancers. In cancer, genes in the glycolytic pathway are overexpressed in more than 70% of human cancer cases spanning 24 different classes of cancers, while overexpression is not observed for other biochemical pathways. Furthermore, the shift to aerobic glycolysis is so extensive that it is now utilized to identify cancer via positron emission tomography (PET) using fluorodeoxyglucose (FDG) as the glycolysis-reporting molecule. FDG PET has an 84-87% sensitivity of detecting cancer and a specificity of 88-93% across all oncology applications. It is now a standard clinical method of cancer detection, staging, and therapeutic assessment, highlighting the pervasiveness of this metabolic shift.

The Warburg effect has not yet been utilized in a drug release mechanism. However, because many diseases exhibit uniquely-altered metabolic pathways, the strategy of synthesizing metabolite-responsive materials has the potential of creating a new class of biomaterials and adding to the toolbox of stimuli-responsive biomaterials. Non-limiting examples of other disease-associated metabolites include succinate, indoxyl sulfate, and glutathione. The strategy of the present invention may be used to generate stimuli-responsive biomaterials specifically tailored for these or other disease associated metabolites.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a metabolite responsive nanoparticle for targeted drug delivery. As a non-limiting example embodiment, the present invention features a lactate responsive polymer hydrogel NP which incorporates the enzyme lactate dehydrogenase (LDH). These NPs are designed to release anti-cancer drugs when exposed to high concentrations of lactic acid. In some embodiments, the enzyme may be attached to the polymer by a polymerizable LDH inhibitor with affinity for the active site of LDH. Upon addition of lactic acid, the monomer inhibitor may be displaced based on the relative affinities of the two substrates. This in turn will lead to an increase in the size of the nanoparticles. The expansion of the particles will be coupled to a release of hydrophobic chemotherapeutics.

The goal of most drug treatment is to be specific and targeted. As such, a therapeutic composition should include a targeting trigger selected in order to achieve specificity. The present invention uses a drug impregnated nanoparticle with a protein having a binding site for a metabolite as a targeting trigger. The selection of targeting trigger is counterintuitive because one of ordinary skill in the art would expect this composition to result in non-specificity of delivery. The reason that one of ordinary skill in the art would expect that the present selection of targeting trigger is counterintuitive is that metabolites are found throughout the body and are not exclusively produced by diseased tissue.

Thus, the prior references teach away from the use of metabolites as the trigger for targeted drug delivery. For example, it is known that the lactate is generated by the body's natural metabolism of glucose and that concentration of lactate in muscle tissue increases during physical exertion. This widespread prevalence of lactate throughout the body teaches away from the selection of lactate as the trigger for targeted drug delivery. However, the present invention uses lactate as an example disease associated metabolite, in spite of its natural occurrence in the body. Such disease associated metabolites may be successfully used for targeted drug delivery, if concentration-dependent responses can be tuned.

Other protein-polymer biomaterials have been synthesized in the past, primarily designed to respond to glucose levels. However, because these hydrogels relied on native protein-substrate interactions, the binding affinities to the triggering molecules were fixed; this resulted in a limited scope of response times and the amount of protein and substrate required. For example, in applications that depend on rapid responses to very small differences in substrate concentrations, such as sensitivity to glucose for managing diabetes, reported two-hour response times to glucose would be inadequate; these long response times were also in the presence of unusually high glucose concentrations that would not be physiologically relevant.

One of the unique and inventive technical features of the present invention is the use of protein engineering to precisely hone the binding affinity and sensing of a molecule to affect the response of a biomaterial. Without wishing to limit the invention to any theory or mechanism, it is believed that the technical feature of the present invention advantageously provides for an alternative highly specific strategy for drug delivery. This metabolite-response approach has not been previously targeted in biomaterials design and drug delivery. The present invention uniquely utilizes protein engineering to precisely hone the binding affinity and sensing of the molecule, which in turn affects the response of the biomaterials of the present invention. This will generate an alternative strategy for drug delivery to tumors, one that could be more specific to tumor tissues. None of the presently known prior references or work has the unique inventive technical feature of the present invention.

It is surprising that protein engineering allows for precise honing of the binding affinity and the sensitivity of the drug release mechanism because of the difference of environment between the interior of the nanoparticles and a solution. Binding constants of proteins are typically measured in solution. However, because binding is influenced by the localized environment, the same protein may exhibit different binding behavior in a nanoparticle from what would be predicted based on the solution-measured binding constant. This unpredictability of binding behavior inside of the nanoparticles teaches away from precision tuning of drug release based on mutant protein binding affinity. However, the present invention shows the successful use of mutant proteins to tune the sensitivity of the nanoparticles to the metabolite. The mutant proteins not only retain their three-dimensional structure when encapsulated within the polymer, but also keep their ability to bind to the metabolite.

BRIEF DESCRIPTION OF THE DRAWINGS

The features and advantages of the present invention will become apparent from a consideration of the following detailed description presented in connection with the accompanying drawings in which:

FIG. 9A shows an electrophoresis image highlighting expression and purification of thermophilic wild type LDH (SDS-PAGE) with pGRO(ES/EL).

FIG. 9B shows a circular dichroism scan of wtLDH.

FIG. 9C shows a thermostability scan of wtLDH which illustrates that the protein does not denature at the NP reaction temperature (~60° C.).

FIG. 9D shows a mass spectrometry readout illustrating high purity in purification with HisPur Ni-NTA affinity column.

FIG. 10A shows a graph and table of enzymatic kinetics of wtLDH and key mutants.

FIG. 10B shows two graphs and a table of enzymatic kinetics of wtLDH and key mutants, with and without FBP.

FIG. 21A shows an image of OxNPs duster. FIG. 21B shows an image of OxNPs with protein bound. FIG. 21C shows a magnification of blue box from FIG. 21B showing discrete LDH particles. FIG. 21D shows a plot profile of selected protein particles.

DESCRIPTION OF PREFERRED EMBODIMENTS

Figure 1:
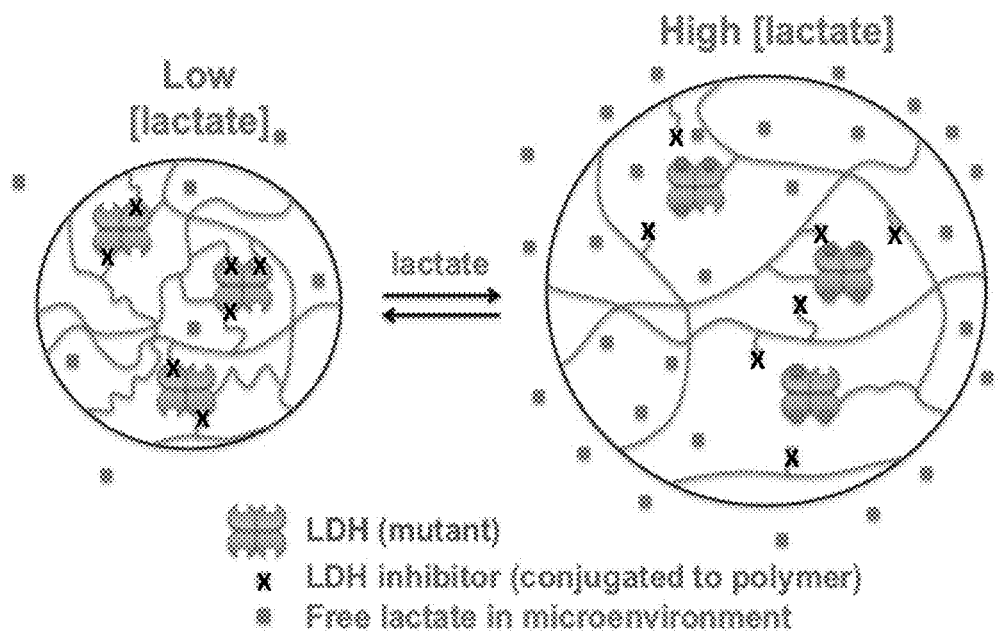
FIG. 1 shows an illustration of a Hybrid protein-polymer material that is responsive to tumor microenvironment. Engineered LDH protein and its polymerizable inhibitor (oxamate) will be incorporated into the hydrogel, with the interaction between LDH and its inhibitor serving as effective non-covalent cross-links. At a sufficiently high lactate concentration, the competition of endogenous lactate and the LDH inhibitor will cause release of the non-covalent cross-links, resulting in gel swelling and subsequently triggered drug release.
Figure 2A:
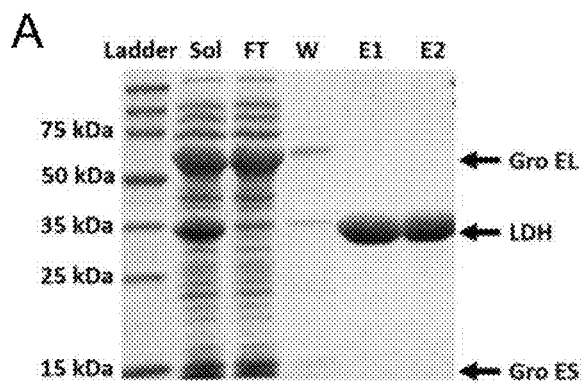
FIG. 2A shows an electrophoresis gel image highlighting the production of recombinant thermophilic wild-type (WT) LDH and a mutant LDH. Expression and purification for wild-type LDH shows that collection of eluent fractions E1 & E2 give purified LDH without bands for endogenous *E. coli* and overexpressed GroEL/ES chaperone proteins. Abbrev.: Sol=soluble fraction, FT=flow-through, W=wash, E1-E2=eluent fractions.
Figure 2B:
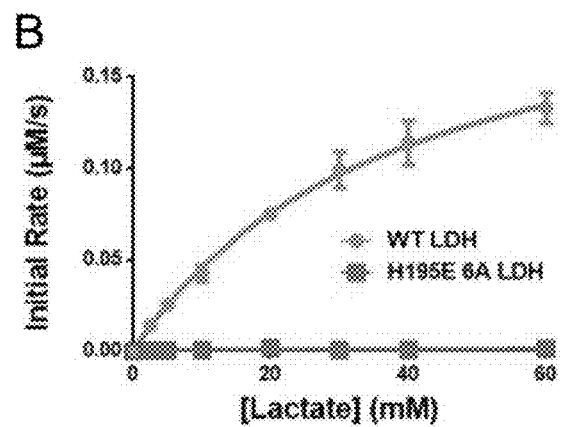
FIG. 2B shows that Purified WT LDH is catalytic, showing that they are structurally intact. Mutant H196E 6A is non-catalytic, as expected.
Figure 2C:
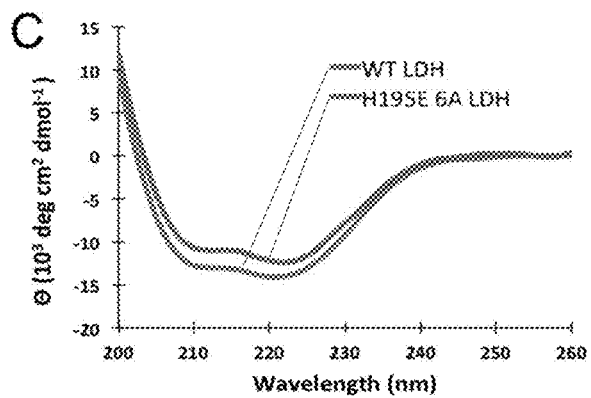
FIG. 2C shows graph of circular dichroism showing folded LDH and mutant LDH with high α-helical structure.
Figure 2D:
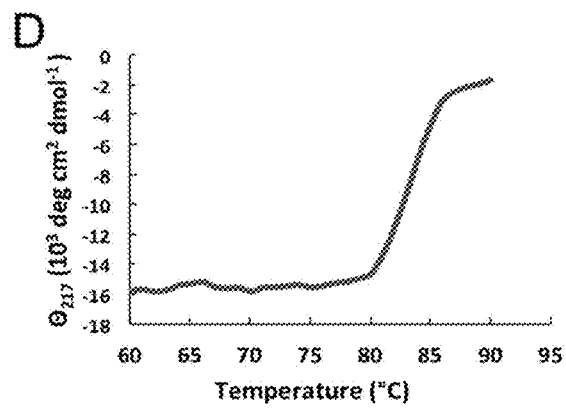
FIG. 2D shows a temperature graph highlighting that LDH proteins are stable and folded up to ~80° C.
Figure 3A:
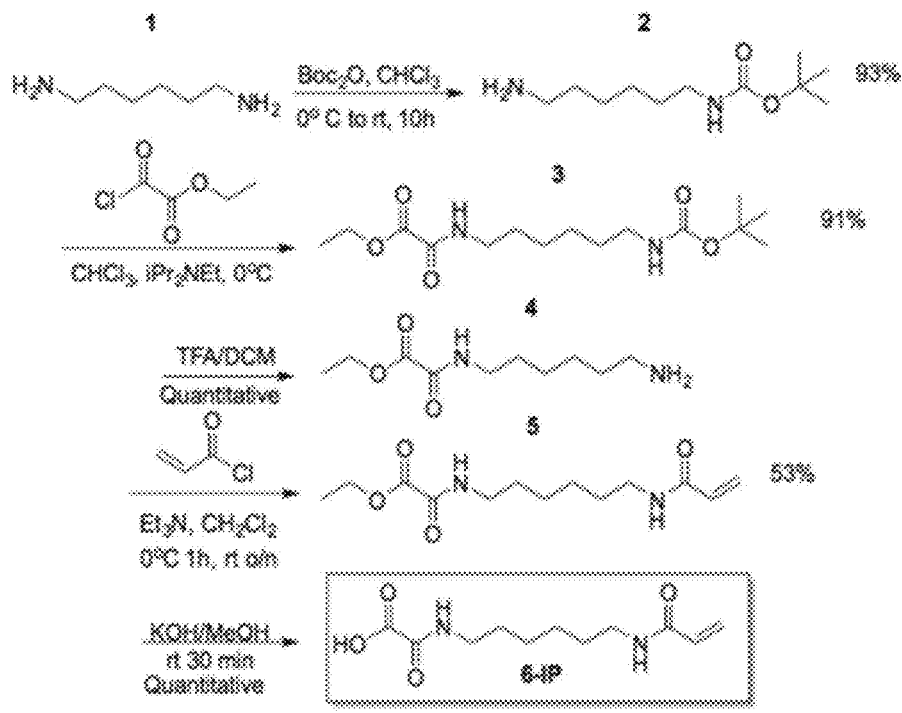
FIG. 3A shows a synthetic scheme for the polymerizable oxamate-based inhibitor monomer (6-IP).
Figure 3B:
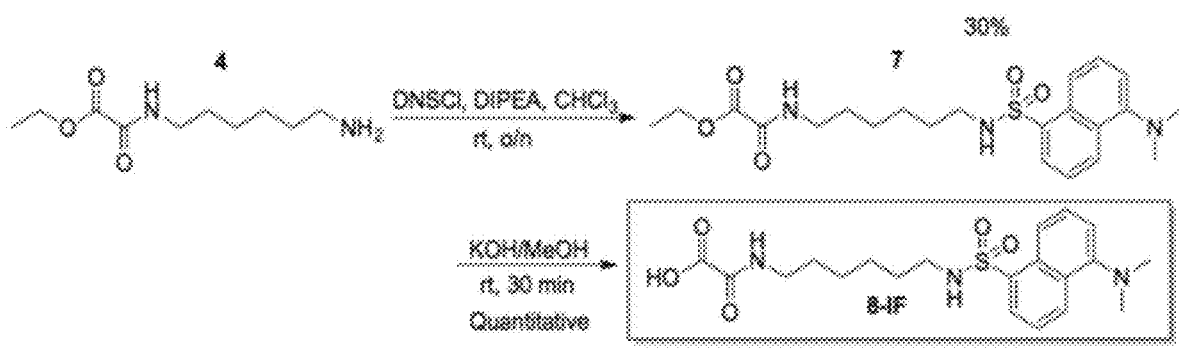
FIG. 3B shows a synthetic scheme for the fluorescent dansylated oxamate inhibitor (8-IF), used to quantify affinity of LDH mutants and for mutagenesis screening.
Figure 4:
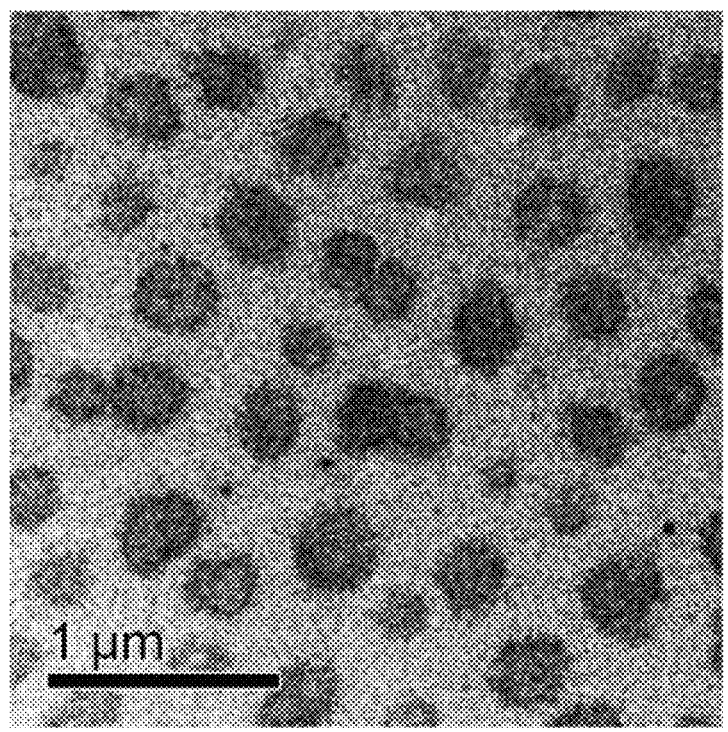
FIG. 4 shows a TEM image of hybrid LDH-polymer NPs. NPs were made with NIPAm, BIS, and WT LDH. NPs were stained with uranyl acetate. Scale bar is 1 µm.
Figure 5:
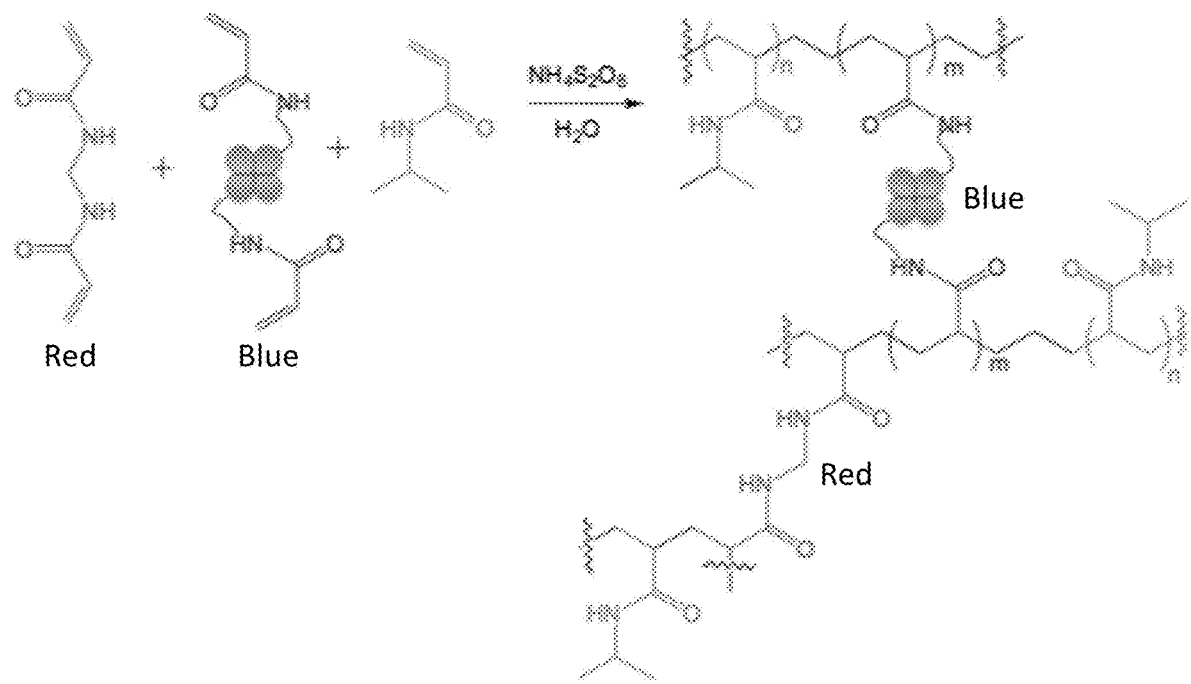
FIG. 5 shows a synthetic strategy for copolymer hydrogel nanoparticles. In blue are non-covalent cross-links, and in red are covalent cross-links. The blue monomer is the inhibitor 6-IP, but for simplicity the entire molecule is not shown. The blue tetramer is LDH (not to scale).

As used herein, "drug" refers to therapeutics such as small molecule drugs, biotherapeutics, antibodies, proteins, peptide delivery, and gene/RNA delivery.

The strategy could be applied to other diseases that are characterized by an altered metabolic state.

Lactate dehydrogenase (LDH). In one embodiment featuring a lactate-responsive material, an enzyme with an active site that natively binds to lactate (lactate dehydrogenase) may be engineered to serve as a lactate-responsive "sensor". LDH catalyzes the interconversion of pyruvate and lactate normally in anaerobic glycolysis. Although mammalian LDH has been studied for physiological relevance, it may not be stable enough to withstand the high temperatures of polymerization. In some embodiments, a thermophilic protein such as LDH from *Bacillus stearothermophilus* may be used. LDH from *Bacillus stearothermophilus* has been widely investigated as an LDH model system and also as a dehydrogenase scaffold on which to build industrially-relevant enzymes using alternative substrates.

Both engineered LDH and an oxamate-based inhibitor may be integrated into the polymer, and free lactate may serve as the competitive substrate to trigger the release of these cross-links for increasing mesh size and releasing entrapped drug molecules. Polymer synthesis highlights another advantage of using LDH from *B. stearothermophilus*; this organism is a thermophile, so its LDH protein exhibits high thermostability. This may be important because elevated temperatures (~60° C.) are typically used for polymerization.

In one embodiment, the present invention may feature a metabolite responsive nanoparticle for drug delivery. As a non-limiting example, the nanoparticle may comprise a polymer hydrogel loaded with a drug and a protein having a binding site for a metabolite. In a selected embodiment, the nanoparticle may additionally comprise a polymerizable inhibitor with affinity for the binding site of the protein. In an embodiment the protein may be conjugated to the polymer hydrogel by one or more covalent bonds. In another embodiment, the inhibitor may be attached to the polymer hydrogel and bound within the binding site of the protein. In yet another embodiment, the nanoparticle may be configured to release the drug when the nanoparticle is exposed to the metabolite. As a non-limiting example, the inhibitor may be displaced from the binding site of the protein when the nanoparticle is exposed to a high concentration of the metabolite relative to normal concentrations of the metabolite, and displacement of the inhibitor may be coupled to release of the drug from the nanoparticle. In further embodiments, the metabolite may bind to the protein at the binding site, thereby causing the nanoparticle to swell and release the drug.

In an embodiment, the protein may be a thermophilic protein, an enzyme, a lactate dehydrogenase (LDH) or a mutant or derivative thereof. In a selected embodiment, the protein may be engineered to eliminate a catalytic activity. As a non-limiting example, a lactate dehydrogenase enzyme may be engineered to bind lactate without catalyzing the reaction of lactate. In some embodiments the protein may be encapsulated within the polymer hydrogel. In some other embodiments, an interaction between the protein and the inhibitor may serve as a reversible cross-linker. In one embodiment, the protein may be an enzyme with a natural binding affinity to lactate. In another embodiment, the metabolite may be lactate. In still another embodiment, the drug may be a hydrophobic chemotherapeutic. In some embodiments, the protein may have a greater affinity for the metabolite than for the inhibitor. In other embodiments, displacement of the inhibitor may be a result of a concentration of the metabolite and not a difference in binding affinity. In some embodiments, a diameter of the nanoparticle may increase when the nanoparticle is exposed to the metabolite or when the inhibitor is displaced.

According to some embodiments, the present invention may feature a protein-polymer biomaterial. As a non-limiting example, the biomaterial may comprise a polymer hydrogel and a protein having a binding site for a metabolite. In some embodiments, the protein may be disposed within the hydrogel. According to selected embodiments, the biomaterial may additionally comprise an inhibitor with affinity for the binding site of the protein. In some further embodiments, the inhibitor may be bound within the binding site of the protein. In still further embodiments, the inhibitor may be displaced with the biomaterial is exposed to the metabolite, and displacement of the inhibitor may cause a swelling of the biomaterial. As a non-limiting example, the metabolite may bind with the binding site of the protein when the biomaterial is exposed to the metabolite, thereby causing the biomaterial to swell.

In a preferred embodiment, the biomaterial may be configured for drug delivery. As a non-limiting example, the polymer hydrogel may be loaded with a drug molecule and the drug molecule may be released from the polymer hydrogel when the hydrogel swells. In one embodiment, competitive binding of the inhibitor and the metabolite may result in gel swelling and subsequent drug release. In some embodiments, both the protein and the inhibitor may be conjugated with the polymer hydrogel. In other embodiments, the inhibitor may be conjugated with the polymer, but the protein is not conjugated with the polymer. Similarly, in some embodiments, the inhibitor may be linked to the polymer hydrogel or bound to the binding site of the protein.

In one embodiment, the present invention may feature a method for drug delivery. As a non-limiting example, the method may comprise providing a metabolite-responsive biomaterial, comprising a protein; loading the biomaterial with a drug; and delivering the loaded biomaterial to a target tissue which comprises a concentration of a metabolite. In a preferred embodiment, the biomaterial may respond to the metabolite and release the drug. In some embodiments, the biomaterial may comprise a polymer hydrogel. In other embodiments, the biomaterial may comprise an inhibitor bound within a binding site of the protein. In still other embodiments, the biomaterial may swell when the inhibitor is displaced.

The present invention may use any of the following strategies: Strategy 1 uses a protein as a "cross-linker" for controlling mesh size, where both the protein and a polymerizable inhibitor of the protein are both conjugated to the polymer. Strategy 2 uses a protein conjugated into the polymer backbone, but no polymerizable inhibitor of the protein. Strategy 3 uses a polymerizable inhibitor in the polymer backbone, but the protein is not conjugated to the polymer.

Strategy 1: Polymer with Both Protein and Inhibitor are Conjugated to the Polymer The present invention features hybrid protein-polymer materials that can release their drug cargo upon encountering the higher lactate concentrations within these tumor microenvironments. In a non-limiting embodiment, the "sensor" for lactate in these materials may be a mutant of lactate dehydrogenase (LDH), an enzyme with a natural binding affinity to lactate. This protein is engineered to eliminate the catalytic activity but may exhibit desired substrate binding profiles for responding to endogenous lactate. Engineered LDH and its inhibitor may be incorporated into the hydrogel, with interactions between LDH and inhibitor serving as reversible cross-linkers. Competitive binding with lactate in the microenvironment may result in gel swelling and subsequently trigger drug release.

In one embodiment, the present invention may feature a LDH inhibitor, for example oxamate, to be incorporated into the polymer to form the switchable cross-linkers. The present invention may also feature other LDH inhibitors or inhibitors of other proteins to be incorporated into the polymer to form switchable cross-linkers. These other inhibitors may provide for a variety of stimuli responsive materials and nanoparticles which function by a variety of mechanisms. In the example of oxamate, it is an inhibitor that is structurally similar to lactate & pyruvate, and has been extensively studied as a drug that disrupts cancer cell proliferation via LDH inhibition. Furthermore, oxamate tethered to an aminohexyl linker can attach to solid substrates while still retaining the LDH-oxamate binding interaction.

In one embodiment, the present invention may feature a method of selecting a mutant protein for use in a metabolite responsive nanoparticle, so as to tune the responsiveness of the nanoparticle. As a non-limiting example, the algorithm for selection of the mutant protein is as follows: the mutants are first screened or selected for appropriate binding constants in solution, they are then expressed and purified, and then incorporated into the polymer matrix. The degree of polymer swelling over different metabolite concentrations will then be determined; this will identify the mutants that can introduce the appropriate response at the desired metabolite concentrations. Encapsulation and release studies of model drugs (e.g., small molecules and biotherapeutics) at the target metabolite conditions from these protein-polymer hybrid materials will be performed. In one embodiment, the mutant protein may be selected based on published mutant binding constants. In another embodiment, the mutant protein may be selected by generating a library of mutant proteins which are attached to solid beads or encapsulated within nanoparticles, and experimentally determining the binding constants of the mutant proteins in this environment.

The present invention may feature stimuli-responsive nanoparticles that respond to changes to internal cross-linking of the hydrogel. Cross-linking influences all aspects of the hydrogel. NP size decreases and NP density increases with an increase in cross-link density. Recent results from the Shea laboratory reveal the degree of swelling of a stimuli-responsive hydrogel NP is inversely correlated with cross-linking. In the present case, cross-linking between the protein and polymer-bound inhibitors will be non-covalent and temporary. The percent swelling will depend on the initial level of cross-linking. Factors that contribute to this include (a) the local concentration of the polymer-bound inhibitor 6-IP, which is controlled by the mole percent of inhibitor on the polymer backbone, (b) amount of additional cross-linker (e.g, bisacrylamide [BIS], ethyleneglycol dimethacrylate [EGDMA], or biodegradable cross-linkers) added to the polymerization, (c) the amount of protein in the NP and the degree of covalent attachments of the protein to the polymer, (d) the protein-inhibitor binding constant KD, (e) the protein-lactate binding constant, and (f) any contributions the polymer backbone itself has on the desired response, for example any intrinsic affinity of the polymer for the protein. Each of these factors can be controlled to some extent. For example, the local "concentration" of an inhibitor is controlled by the stoichiometry of polymerizable monomers used in the polymerization. The inhibitor KD is controlled by the choice of inhibitor and the inhibitor-protein binding which can be modulated and selected by mutagenesis.

To examine the feasibility of drug release from these hydrogels, cargo molecules may be loaded inside the matrix during hydrogel formation. Molecules of different molecular weights and characteristics serve as model drugs, including small molecule drugs (e.g, fluorescein, paclitaxel, doxorubicin), mid-range biomolecules ranging between 4 kDa to 150 kDa (e.g, dextrans at molecular weights 4 kDa, 20 kDa, 70 kDa; lysozyme, BSA, and IgG), and large complexes representative of small nanoparticles with drug loading and cell-targeting abilities (e.g., E2 caged protein, 1700 kDa).

Small molecules and peptides (MW~1500 Da) can diffuse in and out of hydrogel nanoparticles with ease. This ability is necessary to achieve the response needed for the stimulated expansion, as the hydrogel network must be permeable to small hydrophilic molecules (i.e., lactate). In addition, hydrophobic pockets can exist, and can be engineered, in these nanoparticles. This allows sequestration of small, hydrophobic molecules into the hydrogels. Thus, although work by others has shown diffusion of biomacromolecules out of a polymeric matrix when mesh size is on the order of the hydrodynamic diameter, the present invention is unique in that it may allow for tuning of the hydrophobicity as a way to capture hydrophobic small molecule drugs (e.g. doxorubicin, paclitaxel). Therefore, a large range of molecular sizes may be implemented, including those below the anticipated mesh size of the polymer.

Strategy 2: Polymer with Protein Conjugated to it, without Inhibitor

In this strategy, recombinant lactate dehydrogenase (LDH) is conjugated into the polymer backbone, a cross-linker is also used but polymerization occurs without an LDH inhibitor (e.g., polymerizable oxamate inhibitor). Non-limiting examples of the cross-linker include bisacrylamide [BIS], ethyleneglycol dimethacrylate [EGDMA], and biodegradable cross-linkers.

A thermostable recombinant wild-type lactate dehydrogenase (wt-LDH) (with amino acid sequence from thermophilic bacteria *Bacillus stearothermophilus*) was synthesized in *E. coli* and isolated. The stability of the protein at temperatures>60° C. is necessary for nanoparticle (NP) synthesis. Expression and purification of LDH (SDS-PAGE) with pGRO(ES/EL) with large scale enough for NP synthesis was successful. Mass spectrometry showed high purity in purification with a HisPur Ni-NTA affinity column. A circular dichroism thermostability scan of wtLDH showed that the protein does not denature at the NP reaction temperature (~60° C.).

Analysis of wtLDH activity showed that the enzyme is structurally intact and correctly folded. Analysis of wtLDH kinetics showed comparable value to the literature values. Additionally, mutants of LDH can also be made. The activity of the LDH was knocked out with H195E LDH to prevent interconversion of lactate to pyruvate in applicational purposes (binding only, no catalysis, which is desired in our nanoparticles).

NPs can be made with different mutant LDH, and dynamic light scattering (DLS) measurements show thermal responsive behavior of NIPAM-LDH hybrid nanoparticles. TEM images also show comparable size as the DLS measurements. The following NP compositions were synthesized: NP42—99% NIPAM+1% BIS+0.5 mg functionalized wtLDH; NP43—99% NIPAM+1% BIS+0.5 mg functionalized T246A LDH; NP44—99% NIPAM+1% BIS+0.5 mg functionalized H195E LDH; and NP45—99% NIPAM+1% BIS+0.5 mg functionalized 6A LDH. DLS measurements were reproducible with similar sizes for both 25° C. and 37° C. with same composition. TEM images were obtained once with 98% NIPAM+2% Bis with 0.2 mg of wtLDH with size of particle like the size measured from DLS. Conjugated LDH is active within nanoparticles, indicating structural integrity of protein. A kinetic study of wtLDH incorporated NPs showed some activity compared to particles without any wtLDH.

NPs containing different LDH mutants swell to different degrees when lactate is present. A NP31 composition was used as a negative control with 99% NIPAM+1% BIS and without any LDH. NPs with LDH (WT and mutants) incorporated showed response while the NP without LDH did not. Without wishing to limit the present invention, the binding affinity of the lactate to LDH may affect the swelling response profile. The swelling profiles of the nanoparticles with different concentrations of lactate showed that enzyme affinity for the ligand may affect the particle swelling. The data show that NP swelling is correlated with recombinantly changing the protein binding affinity to lactate. This suggests that NP swelling behavior can be tuned by changing binding affinity of LDH to lactate, allowing the ability to tune to different lactate concentrations Material and Methods:
Cloning of LDH DNA of LDH from *B. stearothermophilus* with N terminal His6× tag is purchased from IDT using sequences optimized for *E. coli* expression. DNA is ligated into Blunt Topo vector and transformed into DH5a cells. The transformed cells are grown and miniprepped using Qiagen miniprep kit. The sequences of the wtLDH DNA are confirmed with standard Sanger's sequencing through GeneWiz. wtLDH fragment of wtLDH-TOPO vector is digested with BamHI and NdeI and extracted from a 0.7% agarose gel with GeneJET gel extraction kit. The extracted DNA is ligated into a BamHI- and NdeI-digested pET11a vector. The ligated plasmid is co-transformed into chemically competent BL21(DE3) cells with pGRO7 chaperone protein plasmid.

Site-Directed Mutagenesis

LDH mutants except the 6A LDH were generated using the polymerase chain reaction (PCR) with primers that contained the desired mutations. (Liu, H. and J. Naismith, *An efficient one-step site-directed deletion, insertion, single and multiple-site plasmid mutagenesis protocol*. BMC Biotechnology, 2008. 8(1): p. 91.) The designed primers contained an overlapping region at the 5' end and few non-overlapping region containing the mutation at the 3' end. The template DNA was extended using PCR with the primers resulting in an amplification of DNA containing mutation. The PCR product is digested with DpnI and transformed into chemically competent DH5a. Single colonies are selected and screened by agarose gel electrophoresis and DNA sequencing. After confirming the sequence, the mutant DNA is co-transformed into chemically competent BL21(DE3) cells with pGRO7 chaperone protein plasmid.

Purification of LDH

Single colony of co-transformed BL21(DE3) cells is picked and incubated overnight at 37° C. for 16-18 hrs. The overnight is reinoculated into 1 L of LB culture containing 100 μg/ml ampicillin and 50 μg/ml chloramphenicol. In addition, 1 mM arabinose is added to induce the expression of GroEL/ES chaperone proteins. Once the OD600 of the culture reaches 0.6-0.7, the LDH expression is induced with 1 mM IPTG for 3 hrs and harvested. Harvested cells are resuspended in breaking buffer and lysed in French pressure cell. Cell debris and insoluble fractions were removed using ultracentrifuge and soluble fraction was purified using HIS-Pur Ni-NTA affinity column. Samples of each fractions from the affinity column were run on SDS-PAGE. The elution fractions are combined and buffer-exchanged into phosphate buffer using Zeba Desalting columns. The concentration of the purified LDH was obtained with micro BCA Kit and stored in −80° C.

Kinetics

Enzyme kinetics was measured by absorbance increase at 340 nm in the generation of NADH. All assays were done at 25° C. and in 100 mM triethanolamine hydrochloride buffer following the protocols of Clarke et al. (Clarke, A. R., Wilks, H. M., Barstow, D. A., Atkinson, T., Chia, W. N. & Holbrook, J. J. *An Investigation of the Contribution Made by the Carboxylate Group of an Active Site Histidine-Aspartate Couple to Binding and Catalysis in Lactate Dehydrogenase*. Biochemistry 27, 1617-1622 (1988)]. Enzyme concentration of 100 nM were mixed with 10 mM NAD+ and 20 mM FBP with varying lactate concentrations for the assay. Km and Kcat were determined using GraphPad Michaelis-Menten curve fit.

TABLE 1

Measurement of kinetic parameters for wild type LDH and mutant LDH

|  | Wt-LDH | 6A LDH | T246A LDH | H195E LDH |
|---|---|---|---|---|
| Km (mM) | 38.5 | 120.8 | 2.12 | N.A. |
| Kcat (s−1) | 8.8 | 3.16 | 1.12 |  |
| Kcat/Km | 0.23 | 0.02 | 0.53 |  |

Circular Dichroism Measurements

The tertiary structure and thermostability of WT and mutant LDH were obtained following the protocol of Molino et al. Jasco 810 spectropolarimeter equipped with Jasco Peltier temperature controller (Jasco, Easton, Md.) were used to measure the far-UV circular dichroism (CD). LDH samples were prepared at a concentration of 0.06 mg/ml in 50 mM potassium phosphate and 100 mM NaCl. Samples were scanned between 200-260 nm at 25 C at scanning speed of 10 nm/min in 0.1 pathlength quartz cells. Thermal unfolding was monitored at ellipticity at 217 nm from 60° C. to 90° C. at a heating rate of 1° C./min.

NP Synthesis

Nanoparticles were synthesized following the protocols from O'Brien et al. except the composition of the starting materials. (Brien, O. & Shea, K. J. *Tuning the Protein Corona of Hydrogel Nanoparticles: The Synthesis of Abiotic Protein and Peptide Affinity Reagents*. (2016). doi:10.1021/acs.accounts.6b00125) 0.5 mg of wt and mutant LDHs were incubated with NSA at 37° C. for 1 hr in PBS to introduce a vinyl group for particle conjugation. After incubation, the LDH is desalted to remove unreacted NSA. NIPAm (72 mg), BIS (1 mg), SDS (2 mg), APS (6 mg), and functionalized LDH (0.5 mg) mixed into a round bottom and filled to 10 mL synthesis volume. The air is purged from the mixture using nitrogen gas for 30 min and synthesis was performed at ~60° C. for 1 hr. After synthesis, the mixture is dialyzed in 10,000-14,000 MWCO dialysis tubing for 4 days with excess water (changed twice a day) at 5° C. to remove unreacted or partially reacted monomers. Dynamic Light Scattering (DLS) was used to measure the hydrodynamic diameter of the particles after dialysis.

Swelling Experiment

NPs (0.4 mg/ml) were incubated with 0.5 mM FBP, 5 mM NAD+, and varying lactate concentrations for 30 min at 25° C. After incubation, the hydrodynamic diameters of the NPs were measured with DLS after 2 min of incubation at 37° C. in a quartz cuvette. All measurements were done in triplicates and averaged.

Screening Assay

Mutant screening assay follows similar strategies as protocols described in Hawrani et al. [Hawrani, A. S. El, Sessions, R. B., Moreton, K. M. & Holbrook, J. J. Guided Evolution of Enzymes with New Substrate Specificities. J. Mol. Bio. 97-110 (1996).] Transformed cells were grown on plates containing ampicillin and IPTG to induce expression of mutant LDH. The colonies were lifted onto nitrocellulose filter and dried for 2 min at room temperature. A cutout of Whatman sheet was placed onto a petri dish soaked in buffer I containing 10 mM Tris, 1 mM EDTA, and 4 mg/ml of lysozyme. The lifted nitrocellulose filter with colonies was placed onto (colonies facing up) the petri dish with buffer I and incubated at 30 C for 1 hr. The incubated nitrocellulose filter was placed onto a dried piece of Whatman sheet and washed with buffer I with 1% (v/v) Triton X-100. After washing the colonies, the nitrocellulose filter was placed onto Whatman sheet soaked in buffer I and incubated at 65 C water bath for 30 min to denature the endogenous enzymes. The filer was washed again and sprayed with buffer II (100 mM Tris, pH 8.0 with 5 mM NAD+, 10 mM FBP, 40 mM lactate, 1 mg/ml nitroblue tetrazolium, and 0.5 mg/ml phnazine methosulphate). The coloration of the assay reaction was incubated in room temperature for 3 hours in dark.

In assaying the enzymatically inactive enzymes, instead of using the nitroblue tetrazolium assay solution, a fluorescently tagged analog of lactate was used to determine the binding affinity of the protein. The initial lysis and wash step remained the same as previously described. However, buffer III containing 10 mM Tris, pH 8.0 with 5 mM NAD+, 10 mM FBP, and 1 mM of fluorescent inhibitor was sprayed onto the nitrocellulose filter. The assay was incubated in room temperature for 3 hours in dark and washed with buffer I without the lysozyme. Binding was observed through Alpha-Imager at 360 nm wavelength. The binding strength was obtained using the ImageJ program for total fluorescence intensity.

Strategy 3—Polymer Contains a Conjugated Polymerizable Protein Inhibitor but not Protein Conjugated to the Polymer In this strategy, the polymer is synthesized with an LDH inhibitor (e.g., polymerizable oxamate inhibitor) and a cross-linker (e.g, bisacrylamide [BIS], ethyleneglycol dimethacrylate [EGDMA], biodegradable cross-linkers), but recombinant lactate dehydrogenase (LDH) is not chemically conjugated. Instead, LDH is incorporated into the material by incubation with the polymer. Without wishing to limit the invention to a particular theory or mechanism, the LDH may presumably bind to the polymerizable inhibitor.

Results and Discussion

Synthesis of Polymerizable Oxamate Inhibitor

In this embodiment, a polymerizable oxamate monomer (6) was synthesized and incorporated into NPs, and then these NPs were tested for uptake of LDH and their response to lactate. The synthesis of the polymerizable inhibitor 6 (Scheme 1) begins with the mono-protection of 1,6 hexanediamine with Boc-anhydride. After purifying via flash column chromatography, initial efforts in coupling oxalic acid to the mono-Boc protected diamine proved challenging most likely due to the low electrophilicity of oxalic acid. The synthesis was simplified by switching to a more reactive, electrophilic acid chloride ethyl chlorooxoacetate. The free amine was coupled to ethyl chlorooxoacetate in the presence of Hunig's base. The mono-Boc oxamide 3 was then de-protected with TFA in DCM. Following de-protection, acryloylation of the free amine 4 was performed and 5 was purified via flash column chromatography. The ethyl ester 5 was then hydrolyzed using KOH in MeOH to produce 6.

Scheme 1: Synthetic pathway to polymerizable oxamate derivative 6

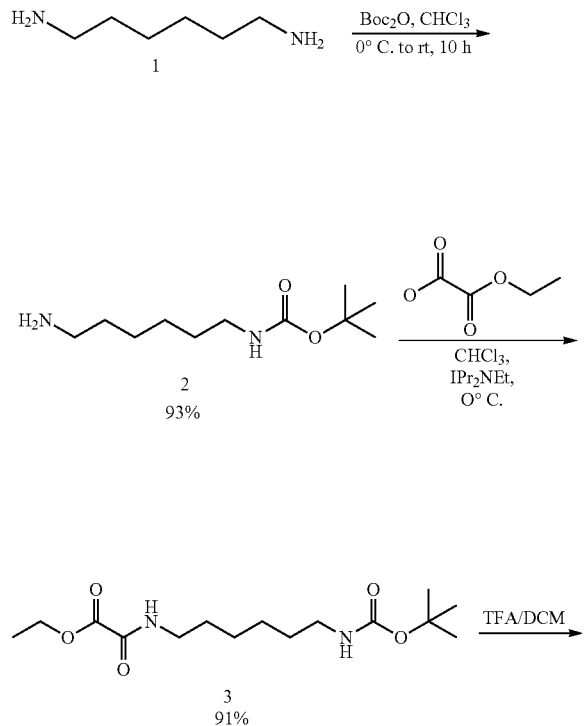

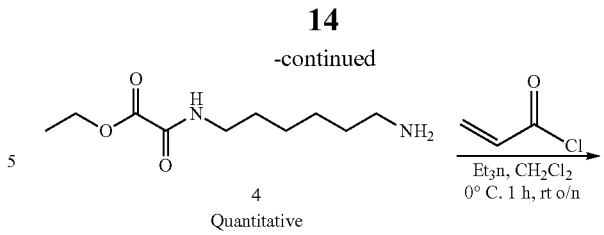

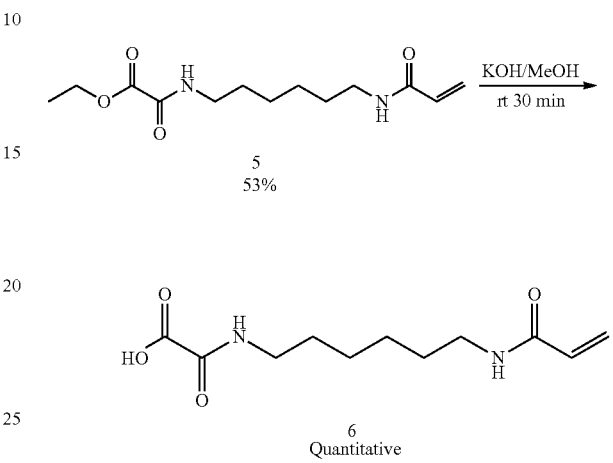

NP Synthesis

The next step was to incorporate 6 into the polymer (Scheme 2). The NP formulation consisted of 2 mol % polymerizable oxamate inhibitor, 2 mol % N,N'-methylenebis(acrylamide) (Bis) as cross-linker, and 96 mol % of N-isopropylacrylamide (NiPAm). NiPAm was chosen due to its lack of nonspecific binding to proteins in serum and its lower critical solution temperature (LCST). NPs were synthesized via a precipitation polymerization in water followed by purification by dialysis for 4 days. Samples were lyophilized to obtain a yield (53%) and characterization by $^1$H NMR (spectra available in Supporting Information). Dynamic light scattering (DLS) was used to determine the hydrodynamic diameter of the particles and their polydispersity (data listed in Experimental Section). The particles were measured above (37° C.) and below (25° C.) the LCST of NiPAm polymers (32° C.). As expected, the particles were solvent swollen below LCST with a size of 338 nm and became hydrophobic above LCST with a size of 148 nm.

Scheme 2: NP synthesis utilizing 2 mol % polymerizable oxamate inhibitor, 96 mol % NiPAm, and 2 mol % Bis.

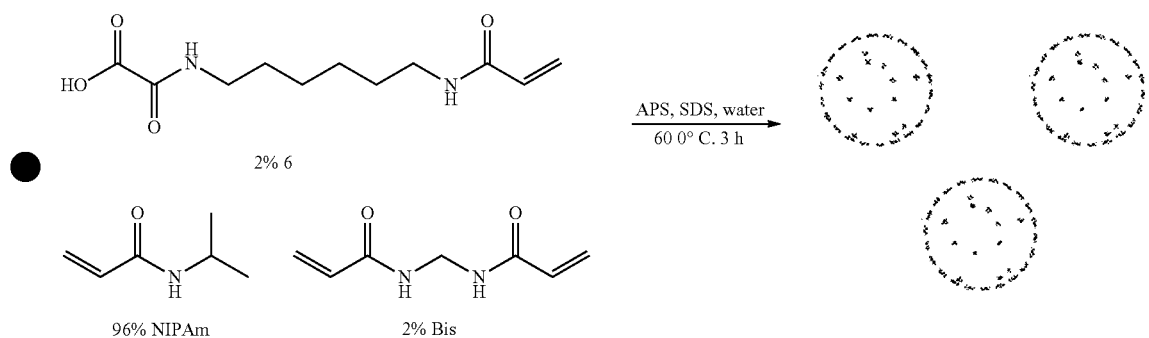

Quantification of LDH Uptake

Following synthesis of NPs, it was necessary to quantify the amount of LDH taken up by NPs. A centrifugation experiment was designed to determine the amount of LDH taken up by NPs. Protein concentration was determined using tryptophan residues which can be measured by fluorescence (Ex 280 nm). The assay is subtractive because the pellet formed after centrifugation should contain NP-protein complexes while the unbound protein will remain in the supernatant. The fluorescence of the supernatant was used to determine how much protein was in the supernatant and the pellet.

Figure 6:
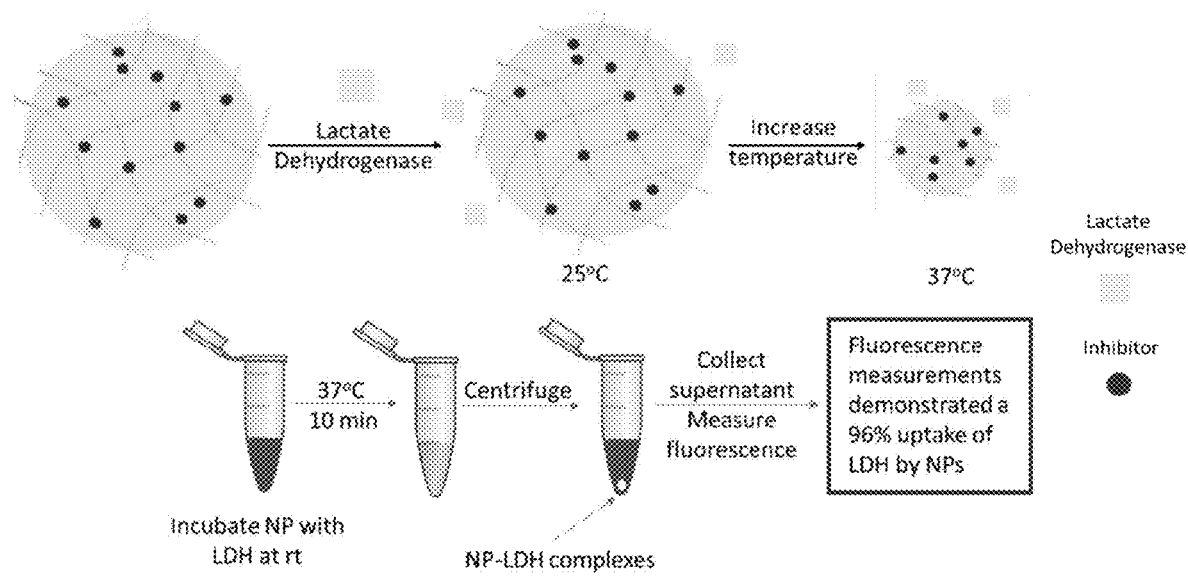
FIG. 6 shows an illustration of a quantification experiment of LDH uptake by NPs. Centrifugation was performed to pull down the NP-LDH complexes leaving the unbound protein free in supernatant.

NPs (0.4 mg/mL) were incubated with LDH (0.35 mg/mL), $NAD^+$ (1 mM), and fructose bisphosphate (FBP) (1 mM) in water before heating then centrifuging. The supernatant was collected to determine the amount of free protein unbound to NP (FIG. 6). An important observation to be noted was that heating the samples did not influence the degree of LDH uptake. Samples that were heated prior to centrifugation bound the same amount of LDH as samples that were not heated previous to centrifugation. NPs bound *Bacillus stearothermophilus* LDH (bsLDH) up to 69% while NPs bound rabbit muscle LDH up to 92%. This difference in binding may be caused by the fact that oxamate is an inhibitor designed for mammalian LDH. Because of this, it has a higher affinity for rabbit muscle LDH than for bsLDH. Control NPs (98% NiPAm and 2% Bis) did not contain any inhibitor and showed at most 1% uptake of bsLDH.

NPs and LDH were incubated at room temperature for 30 min before being heated to 37° C. and centrifuged for 10 min at 14 k rpm. Samples that were not heated continued incubating at rt for an additional 10 min. The supernatant was collected immediately after centrifugation. Fluorescent measurements of the supernatant revealed that upwards of 90% of the LDH in solution was captured by NPs. The pellets formed after centrifuging were re-suspended in water to measure the amount of protein bound to NPs. However, re-suspending the pellets proved to be difficult and required about a week to fully re-suspend uniformly in solution without aggregates. The fluorescence measurements of the re-suspended pellets yielded little signal. This may occur for various reasons. The first may be that protein was damaged during the centrifugation process and there is denatured protein in solution leading to a diluted signal. The second is that upon re-solvating, the polymers swelled and thus pulled apart the protein as the effective cross-linking decreased. This would lead to a weaker fluorescence as the residues dilute or are affected by solvent effects. It is possible that the pellets never re-solvated into distinct particles and there may be aggregates of particles that are solvated. To verify the conformation of LDH remains intact after binding to the polymer, circular dichroism (CD) was performed.

Circular Dichroism Measurements

CD measurements were performed using bsLDH and inhibitor functionalized NPs to study protein-polymer interactions. Each sample was run at room temperature and 37° C. to examine how NPs below and above LCST affects protein folding. The appropriate controls were taken to ensure that bsLDH and NPs below and above LCST did not alter any signals that may have been observed during experimental procedures. NPs show no signal at room temperature or 37° C. while bsLDH maintained its alpha helices. Once the controls were confirmed, NPs incubated with bsLDH were examined.

bsLDH (0.06 mg/mL) and NPs (0.1 mg/mL) were incubated in phosphate buffer (150 mM) with FBP (1 mM) and $NAD^+$ (0.5 mM). $NAD^+$ concentrations were initially 1 mM, but the absorbance interfered with the signal, so the concentration was reduced, and the issue of noise was resolved. Measurements started at 260 nm and stopped at 200 nm. Samples were either incubated at room temperature, incubated then heated to 37° C. and measured, or went through a cycle of heating to 37° C. and cooling back to room temperature (up to two cycles). In all cases, the alpha helices characteristics of bsLDH were maintained. This provides confidence that the interaction between bsLDH and the NPs does not disrupt the conformation of bsLDH.

NP Lactate Responsiveness

Figure 7:
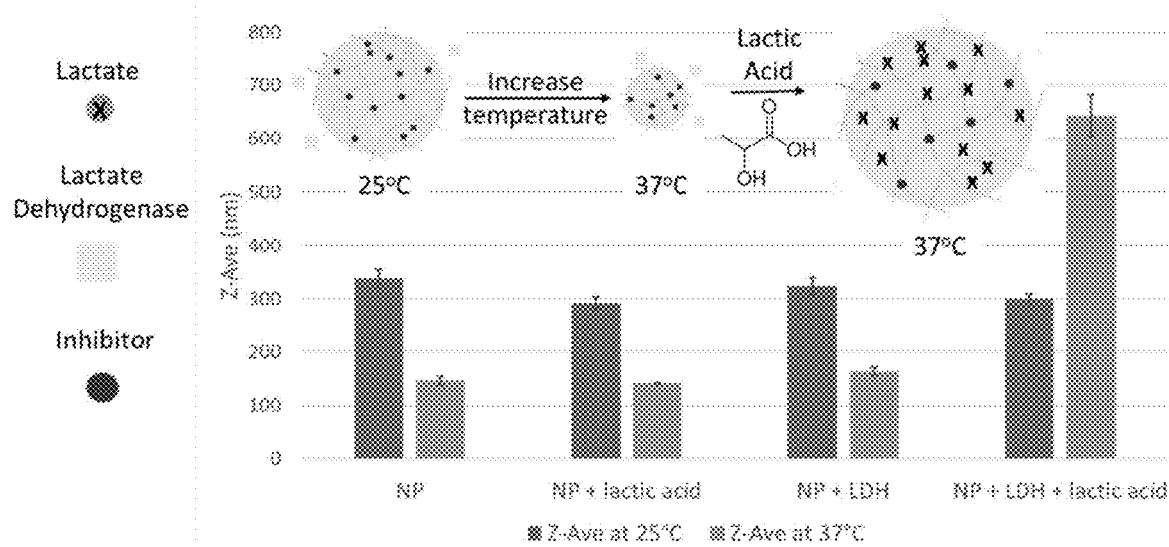
FIG. 7 shows an illustration of the NP response to lactic acid after uptake of LDH. NP, NP+lactic acid, and NP+LDH all show the same trend in particle size above and below LCST. NP+LDH+lactic acid demonstrate particle swelling above LCST.

Upon validation of protein uptake into the NP, the next step was to examine the lactate responsiveness of the system. LDH (0.175 mg/mL), $NAD^+$ (5 mM), and FBP (10 mM) were incubated together at 25° C. for about 1 minute to ensure tetramerization of LDH. Then, NPs were incubated with LDH at 25° C. before measurements began. The experimental results (FIG. 7) show that adding LDH (30 mM) does not affect NP (0.4 mg/mL) size above or below LCST. Lactic acid also had no effect on NP size above or below LCST. There was no apparent change in particle size when lactic acid was added to NP incubated with LDH at 25° C. However, when NP-LDH samples treated with lactic acid were warmed to 37° C., there was a large increase in particle size. When the sample cooled to 25° C., particles exhibited the same size as they did before warming showing the reversibility of this phenomenon. The temperature at which lactic acid was added to NP-LDH complexes did not affect the size of particles obtained at elevated temperatures. Whether the lactic acid was added at 37° C. or 25° C., the large increase in particle size was still observable at 37° C. There was no noticeable difference in size change between adding lactic acid above or below LCST. This demonstrates that the effect of increasing particle size in response to lactic acid at elevated temperatures is independent of the temperature (25° C. or 37° C.) at which the lactic acid is added.

Without wishing to limit the present invention, the NP-LDH complexes swelling in the presence of lactic acid above LCST may be due to osmotic pressure. LDH, like all proteins, is a polyionic species and is encapsulated by the NP. Above LCST, the NP will collapse and bring these charges closer together. However, in the presence of a polyanionic ligand with affinity for LDH such as lactic acid, this adds more charge. As particles collapse more, the distance between charges shrinks and leads to greater repulsive interactions. The swelling may be caused by osmotic pressure as water flows back in to create a solvation shell around the various polyions encapsulated in the NP. This would explain why the phenomenon is reversible once cooling the sample back to room temperature. To further investigate this phenomenon, scanning electron microscopy (SEM) was performed to clarify whether the increase in size was caused by aggregation.

SEM Imaging of NPs

Figure 8C:
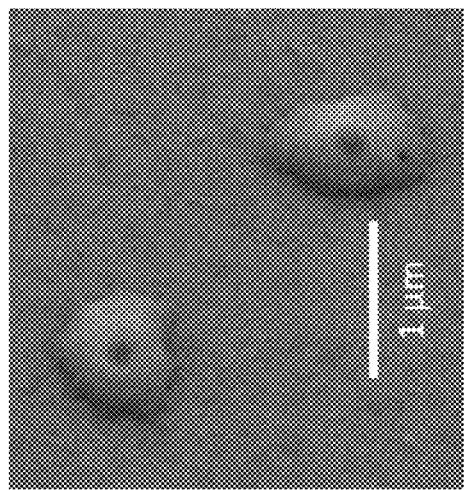
FIG. 8C shows a SEM image of inhibitor containing NPs with LDH and lactic acid.
Figure 8B:
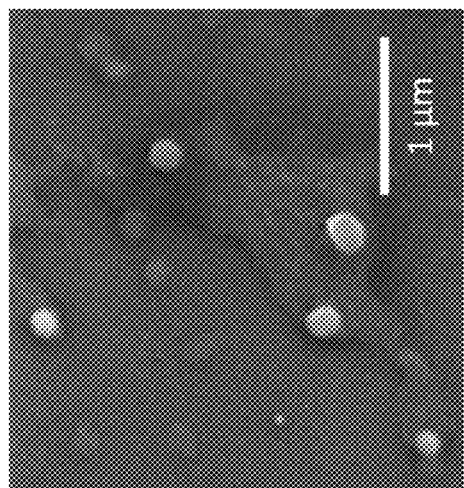
FIG. 8B shows a SEM image of inhibitor containing NPs with LDH.

SEM images were taken to determine morphology and size of particles before addition of LDH and lactate. Images were taken by the Won lab in the Mechanical Engineering Department. Images were first taken of NPs with the same composition as those used to bind LDH (96% NiPAm, 2% Bis, and 2% oxamate inhibitor) but diluted in water to a concentration of 0.04 mg/mL (FIG. 6a). Samples were prepared by drop casting a solution of NP in water (0.04 mg/mL, 10 μL) onto glass slides which were then heated in the oven at 150° C. until dry (1 min). By DLS, NPs exhibited a hydrodynamic size of 310 nm at 25° C. and 140 nm at 37° C. The SEM samples were heated therefore they should exhibit a size close to 140 nm. The SEM images confirm the sizes to reflect those determined by DLS. SEM samples of NP and LDH were also prepared (FIG. 8b). A stock solution of NP (0.4 mg/mL) with LDH (0.175 mg/mL) was diluted to final concentrations of 0.04 mg/mL of NP and 0.0175 mg/mL LDH. The solution was heated to 37° C. followed by drop casting onto glass slides and drying in the oven. The size of NPs in FIG. 8b reflects the DLS measurements taken at 37° C., roughly 140 nm. Samples of NP with LDH and lactic acid (FIG. 8c) were prepared similarly, but a stock solution of NP with LDH was treated with lactic acid before dilution and drop casting. There was no apparent aggregation and particles appeared to exhibit an increase in size. The slightly darker spot in the center may reflect a dimple in the NP. Because these are larger hydrogel particles, they may have sunk in the middle during the drying process.

Experimental Procedures

Methylene chloride and tetrahydrofuran were obtained from a dry Solvent Dispensing System. Chloroform was distilled and kept under nitrogen. Amine bases were freshly distilled over $CaH_2$ from a ketal still. All other commercial reagents were used as received. Reactions were monitored by thin layer chromatography using glass-backed EM Science Silica Gel 60 PF254 Plates. Flash chromatography was performed using EM Science Silica Gel 60 (230-400 mesh). All volatile solvents were removed, in vacuo, under reduced pressure using a Büchi rotary evaporator.

Inhibitor Synthesis

1-Boc-1,6 Hexanediamine 2

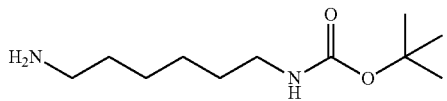

A solution of 1,6-hexanediamine (11 g, 100 mmol) in chloroform (26 mL) was cooled to 0° C. with an external ice bath then treated via dropwise addition over two hours with a solution of Boc anhydride (4.4 g, 20 mmol) in chloroform (20 mL). Reaction was removed from ice and allowed to warm to room temperature. After reacting overnight, the solution was filtered, filtrate concentrated in vacuo, re-dissolved in ethyl acetate, washed with brine (3×), dried over $MgSO_4$, filtered, then concentrated in vacuo. Flash column chromatography was performed and eluted with methylene chloride treated with an equal volume of methanol: ammonium hydroxide solution then concentrated in vacuo to yield 4.5 g (81%) of a thick white oil. $^1H$, $^{13}C$ NMR, and HRMS matched the literature values.

Oxamide Ester 3:

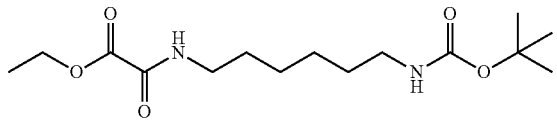 [SMILES: CCOC(=O)C(=O)NCCCCCCNC(=O)OC(C)(C)C]

To a cooled solution of ethyl chlorooxoacetate (0.08 mL, 0.75 mmol) in chloroform (2 mL) at 0° C., a solution of 2 (165 mg, 0.75 mmol) and Hunig's base (0.2 mL, 1.125 mmol) in chloroform (3 mL) was added. Reaction turned from clear to light yellow. After completion by TLC, solution was washed with 0.1 N HCl (1×), washed with DI water (1×), dried over $MgSO_4$, filtered, and concentrated in vacuo. Flash column chromatography was performed eluting with a 4:6 of hexanes to ethyl acetate to yield 156.6 mg (66%) of a light yellow oil. $^1H$ NMR ($CDCl_3$-D+0.05% TMS, 500 MHz): δ/ppm=7.21 (s, 1H, NH), 4.57 (s, 1H, NH), 4.39 (q, 2H, $CH_2$—O), 3.39 (q, 2H, $CH_2$—NH), 3.16 (d, 2H, $CH_2$—NH), 1.5 (m, 12H, $CH_3$), 1.35-1.47 (m, 8H, $CH_2$—$CH_2$); $^{13}C$ NMR ($CDCl_3$-D+0.05% TMS, Cryo 500 MHz): δ 160.9, 156.6, 156.0, 63.3, 40.3, 39.7, 30.0, 29.1, 28.4, 26.3, 26.2, 14.0, 13.9; HRMS (ESI-TOF): m/z calcd for $C_{15}H_{28}N_2O_5$ [M+Na]$^+$ 339.1896; found 339.1892.

Boc Deprotection 4:

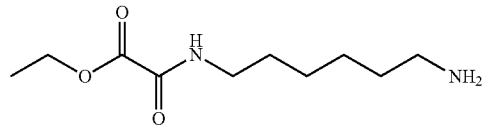

3 (24 mg, 0.079 mmol) was dissolved in methylene chloride (0.3 mL) was treated with TFA (0.2 mL, 2.7 mmol) at room temperature. The reaction was monitored by TLC. Solvent removed to produce a TFA salt, 20 mg (80% yield). $^1H$ NMR ($CDCl_3$-D+0.05% TMS, 500 MHz): δ/ppm=4.42 (q, 2H), 3.43 (m, 2H), 3.17 (m, 2H) 1.79-1.54 (m, 13H); $^{13}C$ NMR (Acetone-D, Cryo 500 MHz): δ 158.8, 158.5, 117.0, 114.7, 62.1, 62.0, 61.9, 54.4, 54.1, 13.35; HRMS (ESI-TOF): m/z calcd for $C_{10}H_{20}N_2O_3$ [M+H]$^+$ 217.1552; found 217.1550.

Acryloylation of the Free Amine 5:

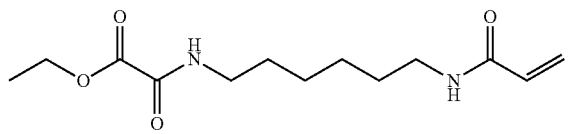 [SMILES: C=CC(=O)NCCCCCCNC(=O)C(=O)OCC]

$Et_3N$ (0.65 mL, 4.5 mmol) was added to compound 4 (125 mg, 0.38 mmol) at 0° C. Then, a solution of acryloyl chloride (36 μL, 0.45 mmol) in $CH_2Cl_2$ (5 mL) was added and stirred for 1 h at 0° C. The reaction then came to rt and left to stir o/n. Reaction was complete by TLC (ethyl acetate, $R_f$=0.25) and washed with $NH_4Cl$ (1×), $NaHCO_3$ (1×), NaCl (1×), then dried over $MgSO_4$, filtered, and concentrated in vacuo. Flash column chromatography in EtOAc was performed to produce 54.8 mg (53% yield). $^1H$ NMR ($CDCl_3$-D+0.05% TMS, 500 MHz): 5/ppm=7.22 (1H, b), 6.33 (dd, 1H, $CH_{sp2}$), 6.16 (dd, 1H, $CH_{sp2}$), 5.69 (dd, 1H, $CH_{sp2}$), 4.41 (d, 1H, NH), 3.39 (q, 2H, $CH_2$—O), 1.65-1.45 (m, 11H, $CH_2$—$CH_2$); 13C NMR ($CDCl_3$-D+0.05% TMS, Cryo 500 MHz): δ 130.9, 126.3, 63.2, 39.5, 39.2, 29.4, 29.0, 26.2, 14.0; HRMS (ESI-TOF): m/z calcd for $C_{13}H_{22}N_2O_4$[M+Na]$^+$ 293.1477; found 293.1475.

Ester Hydrolysis 6:

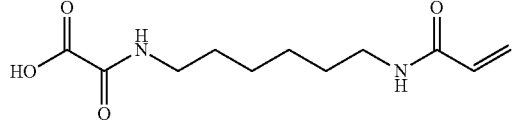 [SMILES: C=CC(=O)NCCCCCCNC(=O)C(=O)O]

KOH (18 mg, 0.32 mmol) was added to a solution of 5 (43 mg, 0.16 mmol) in MeOH (2 mL) at rt. Reaction complete by TLC (ethyl acetate) after 10 min ($R_f$=0). Reaction mixture was acidified with 5 N HCl. Solvent removed to produce a white solid (quantitative yield). $^1$H NMR (CDCl$_3$-D+0.05% TMS, 500 MHz): δ/ppm=8.83 (s, 1H), 8.11 (s, 1H), 6.2 (dd, 1H, CH$_{sp2}$), 6.09 (dd, 1H), 5.58 (dd, 1H, CH$_{sp2}$), 3.11 (m, 4H, CH$_2$) 1.44-1.28 (m, 8H, CH$_2$); $^{13}$C NMR (CDCl$_3$-D+0.05% TMS, Cryo 500 MHz): δ 128.8, 31.9, 29.4, 28.47, 26.1, 22.7, 14.1; HRMS (ESI-TOF): m/z calcd for C$_{11}$H$_{18}$N$_2$O$_4$ [M−H]$^−$ 241.1188; found 241.1188.

Quantification of LDH Uptake

A 1 mL sample of NP (0.4 mg/mL), FBP (1 mM), NAD$^+$ (1 mM), and LDH (0.35 mg/mL) was prepared in nanopure water. Control samples consisted of NP in water and NiPAm NPs (0.4 mg/mL) with LDH (0.35 mg/mL). After LDH was incubated with its cofactors in water (1 min), NP was added. After incubating at rt for 30 min, the samples were heated in a water bath at 37° C. for 10 min followed by centrifugation for 10 min at 14,000 rpm. For samples that were not incubated at 37° C., they incubated at room temperature for an additional 10 min before centrifugation. A white pellet formed at the bottom of the centrifuge tube and the supernatant was collected for fluorescence measurements. Measurements were taken in quartz cuvettes (Stama Cells, 3 mm) on a Cary Eclipse Spectrometer. Excitation was set to 280 nm and emission was measured from 290 nm to 400 nm, RFU measurements were recorded at 342 nm. A calibration curve of LDH was created starting at 0.35 mg/mL ending at 0.01 mg/mL. Pellets were immediately re-suspended in water after the supernatant was removed after centrifugation. The pellets remained at the bottom of the centrifugation tubes. After about a week, the pellets appeared to have fully solvated and were no longer visible.

The number of proteins bound to OxNPs was calculated using the wt/wt ratio of proteins bound to NPs. Using the respective molecular weights (M$_n$ for the OxNPs), the mole to mole ratio was calculated. Using Avogadro's number, the exact number of LDH proteins per OxNP was calculated. Determining density of OxNPs required the molar mass of OxNPs and the Z-Average value to determine the volume. The molar mass of one OxNP was calculated as stated above using M$_n$ and Avogadro's number, this value was then divided by the volume of an OxNP. To determine the percent volume of OxNP taken up by LDH, the volume of 1000 LDH proteins was divided by the volume of OxNP. The volume of LDH was calculated using the mass of one LDH protein divided by its density. The mass of one LDH protein was calculated using the molecular weight of LDH divided by Avogadro's number.

Circular Dichroism of NPs with bsLDH

Measurements were carried out on a Jasco J-380 spectrometer. Continuous scanning was used with a speed of 20 nm/min at increments of 1 nm. Baseline correction was used with a 2 nm bandwidth. All data are an average of three scans. Phosphate buffer (150 mM) was used for baseline correction. Samples (200 µL) consisted of FBP (1 mM), NAD$^+$ (0.5 mM), bsLDH (0.6 mg/mL), and NPs (0.1 mg/mL) in phosphate buffer (150 mM). Measurements were carried out at room temperature and 37° C. For measurements performed at elevated temperatures, samples incubated for 10 min before measuring. Controls were taken of bsLDH and NPs individually. NP controls did not include any cofactors and were taken in phosphate buffer (150 mM). bsLDH controls were performed with necessary cofactors in phosphate buffer (150 mM).

Response of Nanoparticle-Lactate Dehydrogenase Complexes to Lactate

Solutions (1 mL) were made consisting of NP (0.4 mg/mL), FBP (10 mM), NAD$^+$ (5 mM), and LDH (0.4 mg/mL) in water with lactic acid (30 mM) added later. The control sample consisted of NP (0.4 mg/mL) in water. NAD$^+$, FBP, and LDH were incubated together in water for 1 min before adding NP. Samples were incubated at rt for 30 min before taking DLS measurements at 25° C. Measurements were performed in triplicate and the average was taken to determine the hydrodynamic diameter. Samples were then incubated for 3 min at 37° C. before repeating measurements in triplicate. It was visually apparent that particles were above LCST as the solution became turbid. Once samples cooled to rt and became transparent, lactic acid was added. Measurements were taken at 25° C. in triplicate. Samples were then incubated at 37° C. for 3 min and measurements were repeated in triplicate. To test whether the addition of lactic acid was temperature dependent, a separate set of experiments were performed in which lactic acid was added at 37° C. to pre-mixed NP-LDH samples. The same procedure as above was performed except NP-LDH solutions were not allowed to come to rt before lactic acid was added. Measurements were taken immediately at 37° C. The hydrodynamic diameter of NP was the same regardless of whether lactic acid was added at 25° C. or 37° C.

SEM of Inhibitor Functionalized NPs

Samples were prepared by drop casting a solution of NP in water (0.04 mg/mL, 10 µL) onto glass slides which were then heated in the oven at 150° C. until dry (1 min). A stock solution of NP (0.4 mg/mL) with LDH (0.175 mg/mL) was diluted to final concentrations of 0.04 mg/mL of NP and 0.0175 mg/mL LDH. The solution was heated to 37° C. followed by drop casting onto glass slides and drying in the oven. Samples of NP with LDH and lactic acid were prepared similarly, but a stock solution of NP with LDH was treated with lactic acid before dilution and drop casting. Each dilution of LDH contained the appropriate concentrations of the cofactors FBP (10 mM) and NAD$^+$ (5 mM).

In summary, a polymerizable oxamate inhibitor 6 was successfully synthesized and incorporated into lightly crosslinked NPs. LDH was efficiently incorporated into NPs. Equilibrium dialysis was performed to determine capacity, but due to inconsistencies caused by possible protein aggregation and precipitation during the experiment, capacity was not able to be determined. CD was used to demonstrate that LDH maintains its conformation after binding to NPs. NPs containing LDH showed a large swelling response in the presence of high lactic acid concentrations. After treatment with lactic acid below LCST, NPs containing LDH behave normally and remain the same size as without lactic acid. Above the LCST, lactic acid treated NP-LDH complexes swell to almost twice the size as at room temperature. SEM images validated that this was not due to aggregation.

Transmission electron microscopy (TEM) may be used to image where LDH binds in the NP. Preliminary work has been done to synthesize gold NPs which will be coupled to LDH. These Au NP-LDH complexes will be incubated with inhibitor containing NPs followed by TEM imaging. Methods of incorporating a cancer therapy into the polymer have been explored. These results, although preliminary, have shown hydrophobic domains within NPs where hydrophobic drugs may be stored. Investigating the ability for LDH-NPs to release a drug will provide valuable data to support this targeted therapy.

In some embodiments, the present invention features a nanoparticle for drug delivery, such as a nanoparticle configured to release an encapsulated drug in response to a metabolite. As a non-limiting example, the nanoparticle may comprise: a polymer hydrogel; a drug; a protein having a binding site for the metabolite; and an inhibitor with affinity for the binding site of the protein. In some embodiments, the drug may be encapsulated within the polymer hydrogel. In other embodiments, the protein may be encapsulated within the polymer hydrogel. In still other embodiments, the inhibitor may be covalently attached to the polymer hydrogel and bound within the binding site of the protein.

In one embodiment, the nanoparticle may be configured to be displaced from the binding site of the protein when the nanoparticle is exposed to a high concentration of the metabolite relative to a normal concentration of the metabolite, and displacement of the inhibitor may be configured to cause release of the drug from the nanoparticle. As non-limiting examples, the high concentration may be about 1.5, 2, 2.5, 3, 3.5, 4, 4.5, 5, 6, 7, 8, 9, 10, 15, 20, 25, 30, 35, 40, 45, 50, 60, 70, 80, 90, 100, 120, 140, 160, 180, 200, 250, 300, 350, 400, 450, 500, 600, 700, 800, 900, 1000, 1200, 1400, 1600, 1800, 2000, 2500, 3000, 3500, 4000, 4500, 5000, 6000, 7000, 8000, 9000, 10,000, 50,000, 100,000, 500,000, 1,000,000, 5,000,000, 10,000,000, or greater than 10,000,000 times the normal concentration.

In some embodiments, the metabolite may be associated with a disease, a tumor, or a cancer. As a non-limiting example, the disease, tumor, or cancer may cause a higher concentration than a normal concentration of the metabolite in a localized area near the disease, tumor, or cancer. In some embodiments, the protein may be a thermophilic protein. As a non-limiting example, the protein may be lactate dehydrogenase (LDH) or a mutant or derivative thereof, and the metabolite may be lactate.

In some embodiments, the drug may be a hydrophobic or a hydrophilic chemotherapeutic. As a non-limiting example, the hydrophobicity of the drug may be tuned so as to allow for encapsulation within the nanoparticle until desired release of the drug. In some embodiments, the protein may have a greater affinity for the metabolite than for the inhibitor. As a non-limiting example, this difference in affinity may allow the protein to selectively bind to the metabolite and release the inhibitor. In some embodiments, the protein may have about 1.5, 2, 2.5, 3, 3.5, 4, 4.5, 5, 6, 7, 8, 9, 10, 15, 20, 25, 30, 35, 40, 45, 50, 60, 70, 80, 90, 100, 120, 140, 160, 180, 200, 250, 300, 350, 400, 450, 500, 600, 700, 800, 900, 1000, 1200, 1400, 1600, 1800, 2000, 2500, 3000, 3500, 4000, 4500, 5000, 6000, 7000, 8000, 9000, 10,000, 50,000, 100,000, 500,000, 1,000,000, 5,000,000, 10,000,000, or greater than 10,000,000 times the affinity for the metabolite as for the inhibitor.

In some embodiments, the protein may be conjugated to the polymer hydrogel by one or more covalent bonds, or non-covalently held within the polymer hydrogel. In some embodiments, an interaction between the protein and the inhibitor may serve as a reversible cross-linker such that the nanoparticle is more crosslinked when the inhibitor is bound by the protein. In some embodiments, the protein may be engineered to eliminate a catalytic activity.

In one embodiment, the present invention features a metabolite responsive nanoparticle for targeted drug delivery to treat a condition associated with a metabolite. As a non-limiting example, the nanoparticle may comprise: a polymer hydrogel; a drug encapsulated within the polymer hydrogel; and a protein encapsulated within the polymer hydrogel, having a binding site for the metabolite. In desired embodiments, the nanoparticle may be configured to release the drug when the nanoparticle is exposed to the metabolite, or to a higher concentration of the metabolite than a normal concentration of the metabolite.

In some embodiments, the protein may be a mutant protein selected for a binding affinity for the metabolite, which may be greater or less than a binding affinity of the non-mutant protein. In some embodiments, the protein may be conjugated to the polymer. In some embodiments, the binding site may be configured to bind the metabolite, thereby causing the nanoparticle to swell and release the drug. As a non-limiting example, the nanoparticle may swell about 1, 2, 3, 4, 5, 6, 7, 8, 9, 10, 12, 14, 16, 18, 20, 25, 30, 40, 50, 60, 70, 80, 90, 100, 120, 140, 160, 180, 200, 250, 300, 400, 500, 600, 700, 800, 900, 1000, or more than 1000 percent.

In some embodiments, the nanoparticle may additionally comprise an inhibitor with affinity for the binding site of the protein, bound within the binding site of the protein. As a non-limiting example, the inhibitor may be configured to be displaced by the metabolite when the nanoparticle is exposed to the metabolite, and displacement of the inhibitor may be configured to cause swelling of the polymer hydrogel and consequent release of the drug. In some embodiments, the inhibitor may be conjugated with the polymer hydrogel.

In some embodiments, the metabolite may comprise a charged molecule and wherein the nanoparticle is configured to bind multiple metabolite molecules and consequently swell. As a non-limiting example, the nanoparticle may swell due to molecular interactions of the metabolites, such as electrostatic repulsion.

In one embodiment, the present invention may feature a method for targeted drug delivery to a target tissue having a diseased condition. As a non-limiting example, the method may comprise: providing a metabolite-responsive biomaterial, comprising a protein with a binding site for a metabolite associated with the diseased condition; loading the biomaterial with a drug; and delivering the loaded biomaterial to a target tissue. In some embodiments, the target tissue may comprise a concentration of the metabolite, or a higher concentration of the metabolite than a normal concentration of the metabolite. In some embodiments, the biomaterial may respond to the metabolite and release the drug to the target tissue. In some embodiments, the biomaterial may further comprise an inhibitor bound within the binding site of the protein.

Example 1: The Following Non-Limiting Example Provides a Description of One Embodiment of the Present Invention Stimuli responsive polymers are an efficient means of targeted therapy. Compared to conventional agents, they increase bioavailability and efficacy. In particular, polymer hydrogel nanoparticles (NPs) can be designed to respond when exposed to a specific environmental stimulus such as pH or temperature. However, targeting a specific metabolite as the trigger for stimuli response could further elevate selectivity and create a new class of bioresponsive materials. The present invention features an N-isopropylacrylamide (NIPAm) NP that responds to a specific metabolite characteristic of a hypoxic environment found in cancerous tumors. NIPAm NPs were synthesized by copolymerization with an oxamate derivative, a known inhibitor of lactate dehydrogenase (LDH). The oxamate functionalized NPs (OxNP) efficiently sequestered LDH to produce an OxNP-protein complex. When exposed to elevated concentrations of lactic acid, a substrate of LDH and a metabolite characteristic of hypoxic tumor microenvironments, OxNP-LDH complexes swelled (65%). The OxNP-LDH complexes were not responsive to structurally related small molecules. This work demonstrates a proof of concept for tuning NP responsiveness by conjugation with a key protein to target a specific metabolite of disease.

Drug delivery has been a high priority for researchers in academia and industry alike. Challenges arise from solubilizing drugs, maximizing bioavailability, and ensuring selectivity toward the tissues and organs that are to be treated. However, combining these traits into a single vehicle remains elusive and has been a driving force for research. Methods devised to address these problems include developing stimuli-responsive materials. This strategy addresses the challenges of selectivity and if designed appropriately, can help increase bioavailability.

Various strategies have been investigated including systems responsive to changes in pH, reducing or oxidizing environments, disease associated enzymes or small molecules, hypoxic environments, mechanical cues, and temperature. However, the relatively low incidence of clinical success would suggest there are still opportunities to improve performance. Other methods draw inspiration from biology. Protein-polymer conjugates have made an impact in the scientific community as an attractive approach to address drug delivery. These strategies consist of non-covalent, covalent, and supramolecular interactions between polymers and proteins. Some examples involve protein cages, formation of polymer micelles around proteins, and synthesis of nanoparticles incorporating proteins into the backbone. All of these strategies have been used to enhance the success and selectivity of delivering biological agents as well as drugs.

The versatility of nanoparticles allows for a range of approaches to be employed. Protein-nanoparticle complexes are of particular interest as treatments for various diseases, especially cancer. The stimuli response of protein-nanoparticle complexes has depended on many of the previously mentioned strategies. These studies have included adenosine-5'-triphosphate (ATP) and glucose responsive systems. Both the ATP and glucose systems rely on a concentration gradient or an intra- and intercellular difference in concentration of these molecules. The specificity of these systems is lacking in the sense that ATP and glucose are found throughout the body. High local concentration of a specific molecule or metabolite that is a signature of a disease can provide a chemospecific target for therapeutic intervention. However, there remains a compelling need to develop a responsive polymer-protein conjugated system designed around a specific disease associated metabolite. Designing a protein-nanoparticle complex that responds to a metabolite of disease could provide an effective solution to the issue of selectivity. By focusing on a molecule or metabolite that has distinctively high concentrations in the local area of disease, side effects can be minimized while maximizing therapeutic effects.

There have been many studies describing the Warburg effect in cancer progression. This phenomenon describes an accumulation of lactate, leading to a decrease in pH within the cancer microenvironment. The phenomenon is attributed to cancer cells that predominantly utilize anaerobic glycolysis instead of oxidative phosphorylation. Cancer usually exists under low oxygen, or hypoxic, conditions so cells must compensate for this impediment to energy production. This leads to a lactate concentration higher than what is found under normoxic conditions. Anaerobic glycolysis is performed in healthy tissues as well, most notably during exercise when a build-up of lactic acid occurs. Healthy tissues have lactate concentrations between 0.5-2 mM, while concentrations in tumor tissues range from 10-20 mM and up to 40 mM. The almost ten-fold increase in lactic acid lowers the pH from 7.4 to 6.0-7.0 an effect that has been taken advantage of by designing polymers that release anti-cancer drugs under acidic conditions. However, there are organs with regions of low pH that are not associated with cancer, most notably the stomach and kidney. A more chemospecific trigger, such as one that responds to high lactate concentrations, would be more effective.

The present invention features hydrogel nanoparticles (NP) that are responsive to lactate at physiologically relevant concentrations. To achieve this, a known inhibitor of lactate dehydrogenase (LDH), oxamate, was incorporated into the backbone of a hydrogel polymer. The polymer bound oxamate was used to bind LDH, present as a homomeric tetramer, non-covalently to the polymer and function as a cross-linker between the polymer NP and LDH. N-isopropylacrylamide (NIPAm) was utilized as the base monomer. NIPAm was chosen due to its low affinity for plasma proteins, this minimizes any non-specific binding of proteins other than the one of interest. NIPAm polymers exhibit a lower critical solution temperature (LCST) at approximately 32° C. Below this temperature, the polymer is solvent swollen. Increasing the temperature beyond 32° C. desolvates the particle, leading to a volume reduction. The design strategy was to incorporate LDH into the polymer in its solvent swollen state (<32° C.) before raising the temperature to physiological conditions.

Figure 16:
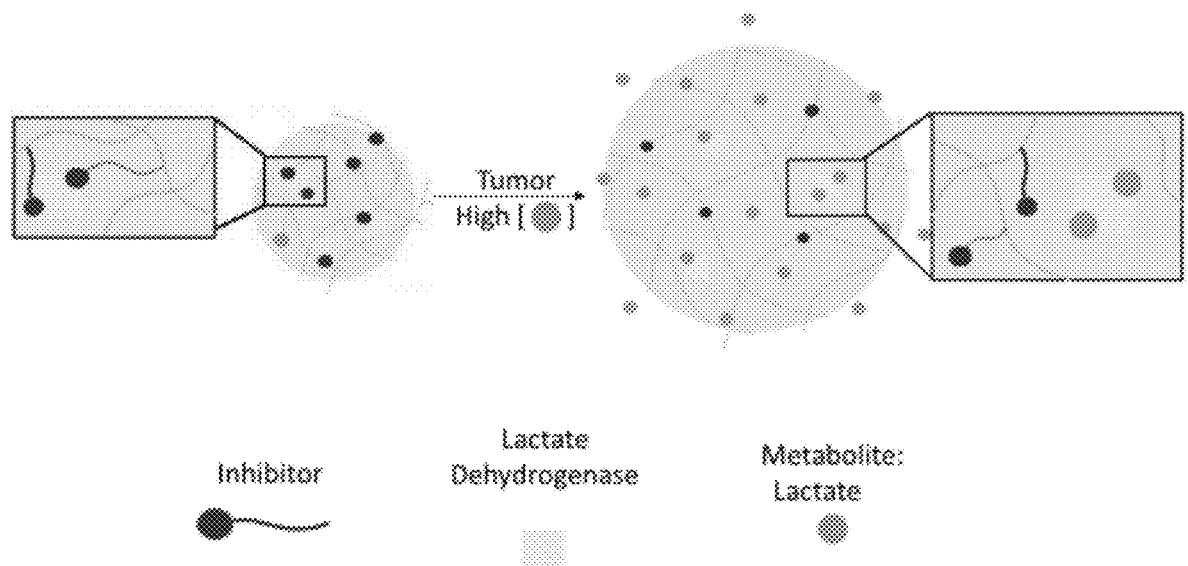
FIG. 16 shows an illustration of a lactate responsive nanoparticle. An inhibitor for LDH is incorporated into the NP. When LDH is introduced, the inhibitor acts as a cross-linker between the particle and protein leading to a decrease in NP size. Once the complex is introduced to lactate, the inhibitor is displaced and the cross-linking is eliminated. This leads to a swelling of the particle.

The LDH used was based on the protein sequence of *Bacillus stearothermophilus* LDH, a thermally stable and well characterized protein that would be compatible with experimental conditions. LDH is a homomeric tetramer with four binding sites and provides a nexus for cross-linking by the polymer-bound oxamate (FIG. 16). This enzyme converts pyruvate into lactate, this is done at higher than normal rates within the tumor microenvironment so the cancer cells can utilize lactate fermentation. However, this enzymatic reaction is reversible, and lactate can be converted back into pyruvate with the same enzyme. The polymer-bound oxamate will non-covalently bind LDH; when more than one oxamate binds to the homomeric tetramer, the result is cross-linking. These cross-links will be competitively displaced by lactate upon entering an environment with elevated lactate levels. The decreased cross-linking of the polymer to LDH endows the particle with a lactate responsiveness that results in NP swelling. At appropriate loadings of inhibitor and LDH, one can tune the lactate responsiveness of the NP to the relevant physiological range of lactate in the local cancer environment.

EXPERIMENTAL

OxNP Characterization

DLS was run using OxNPs diluted 10-fold into nanopure water. Samples at 37° C. were equilibrated for 2 min before measuring. Molecular weight of nanoparticles was determined using SEC-MALS (Malvem Viskotek GPC/SEC triple detection system). The system was run in PBS (10 mM phosphate, 50 mM NaCl). The column (Viskotek A7000) was heated to 30° C. and the system was calibrated to a 500 kDa pullulan standard. Nanoparticle samples were prepared by dialyzing in PBS overnight. The OxNP sample was diluted into PBS (2.5 mg/mL) and injected onto the column. Injections of 40 µL were used with a flow rate of 1 mL/min. The $M_n$ was determined to be $2.276 \times 10^8$ and $M_w$ was $2.863 \times 10^8$ with a PDI of 1.26.

LDH Kinetics

Protocols for determining $K_{cat}$ and $K_m$ of LDH were based on previous studies by Clarke et al.[48] Enzyme kinetics were measured by absorbance increases at 340 nm in the generation of NADH. All assays were done at 25° C. and in 100 mM triethanolamine hydrochloride buffer. Enzyme at 100 nM was mixed with 10 mM NAD$^+$ and 20 mM FBP with varying lactate concentrations. The initial slope of the absorbance vs. time was obtained for a range of lactate concentrations. This initial slope vs. concentration of lactate was plotted in GraphPad Prism and kinetic parameters ($K_m$ and $k_{cat}$) were determined using a non-linear curve fit to the Michaelis-Menten equation.

Response of OxNPs to Small Molecules

Solutions (1 mL) were made consisting of OxNP (0.4 mg/mL) and small molecules (10 mM) in nanopure water. Samples incubated for 5-10 min at rt before being measured. DLS measurements at 25° C. were performed in triplicate and the average was taken to determine the hydrodynamic diameter. Samples were then incubated for 2 min at 37° C. before repeating measurements in triplicate. It was visually apparent that particles were above LCST as the solution became turbid with turbidity increasing with the size of the particles.

The size change was converted to percent change in volume using the size of OxNP as the standard. This was determined by calculating the volume of OxNPs with small molecules based on their Z-Average. This was subtracted from the volume of OxNP and divided by the volume of OxNP using Equation 1. OxNP percent change in volume was set as 0.

$$\% \text{ Change in volume} = \frac{(\text{Volume of } OxNP \text{ with Small Molecule} - \text{Volume of } OxNP)}{\text{Volume of } OxNP} \quad \text{Equation 1}$$

Response of OxNP-LDH Complexes to Small Molecules

Solutions (1 mL) were made consisting of OxNP, FBP (1 mM), NAD$^+$ (1 mM), and LDH (0.175 mg/mL). The control sample consisted of NIPAm NPs (0.4 mg/mL) in water. NAD$^+$, FBP, and LDH were incubated together in water for 1 min before adding NP. Samples were incubated at rt for 10 min before taking DLS measurements at 25° C. Measurements were performed in triplicate and the average was taken to determine the hydrodynamic diameter. Samples were then incubated for 2 min at 37° C. before repeating measurements in triplicate. It was visually apparent that particles were above LCST as the solution became turbid. OxNP-LDH complexes containing small molecules (10 mM) were prepared in a similar manner as above except small molecules were added at rt before measuring. The same procedure was also followed for their DLS measurements. To test whether the addition of lactic acid was temperature dependent, a separate set of experiments were performed in which lactic acid was added at 37° C. to pre-mixed OxNP-LDH samples. The same procedure as above was performed except OxNP-LDH solutions were not allowed to come to rt before lactic acid was added. Measurements were taken immediately at 37° C. The hydrodynamic diameter of NP was the same regardless of whether lactic acid was added at 25° C. or 37° C. The percent change in volume is detailed by Equation 2.

$$\% \text{ Change in volume} = \frac{(\text{Volume } OxNP\ LDH \text{ with Small Molecule} - \text{Volume } OxNP\ LDH)}{\text{Volume } OxNP\ LDH} \quad \text{Equation 2}$$

SEM of Inhibitor Functionalized NPs

A stock solution of OxNP (0.4 mg/mL) containing LDH (0.175 mg/mL), FBP (10 mM), and NAD$^+$ (5 mM) was diluted ten-fold to a final concentration of 0.04 mg/mL OxNP and 0.0175 mg/mL LDH. OxNP samples were prepared by drop casting a solution of OxNP in water (0.04 mg/mL, 10 μL) onto glass slides which were then heated in the oven at 150° C. until dry (1 min). OxNP-LDH complexes were prepared by combining OxNP with LDH and coenzymes before diluting to concentrations previously mentioned. The solution was heated to 37° C. followed by drop casting onto glass slides and drying in the oven. Samples of OxNP with LDH and lactic acid were prepared similarly, but a stock solution of OxNP with LDH was treated with lactic acid before dilution and drop casting. The samples were sputter coated with a thin conductive layer (5 nm) of gold/palladium alloy (Polaron SC7620) to render the surface of the NP electrically conductive for SEM imaging. Morphological characterization from the SEM (FEI Quanta 3D) was conducted using an electron voltage of 5 kV and a current of 53 pA.

CryoTEM of OxNP-LDH Complexes

Cryo-TEM samples were prepared by depositing 3 μl sample on a 200 mesh Cu grids with lacey carbon films (Electron Microscopy Sciences). All TEM grids were surface plasma treated for 20 seconds using a Gatan Solarus Advanced Plasma Cleaning System 950 prior to use. An automated vitrification robot (Leica EM GP) was used for plunge vitrification in liquid propane. Cryo-TEM studies were performed on the JEOL JEM 2100F operated at 200 kV, 2k×2k Gatan CCD camera. Gatan DigitalMicrograph. ImageJ was used for TEM image analysis.

Results and Discussion

Synthesis of Polymerizable Oxamate Derivative

To impart NPs with affinity for LDH, an oxamate derivative was selected as a non-covalent inhibitor. Oxamate is a competitive inhibitor of pyruvate for LDH with a similar $K_m$ as pyruvate for LDH (0.6 mM). Since attachment of the inhibitor to a polymer backbone can restrict access to the LDH active site, a six carbon atom tether was selected for the oxamate inhibitor. The choice was based on the successful use of a solid-phase tethered oxamate derivative to purify LDH by affinity chromatography. In the chromatographic application, the oxamate moiety was coupled to a 1,6-hexanediamine spacer bound to a Sepharose bead. Drawing from these results, an α,ω-1,6-diamine was functionalized with the oxamate group at the alpha position and an acrylamide at the omega position. In this design, the alpha position can bind to LDH while the omega position can be covalently incorporated into the polymer backbone.

OxNP Synthesis

The next step was incorporation of 6 into a NIPAm based polymer (Scheme 2). The oxamate functionalized NP (OxNP) formulation consisted of 2 mol % polymerizable oxamate inhibitor 6, 2 mol % N,N'-methylenebis(acrylamide) (Bis) as cross-linker, and 96 mol % NIPAm. Equal reactivity of NIPAm and the oxamate derivative was assumed since both are N-substituted acrylamides. Under these conditions, the feed ratios should reflect the actual incorporation of the monomers in the polymer with random distribution of the oxamate derivative. This is further supported by the high yield of the polymerization (90%). The OxNPs contain an additional permanent cross-linker, 2 mol % Bis. This low-level of covalent cross-linking was included to ensure uniformly sized NPs form but low enough to remain responsive to changes in non-covalent cross-linking between the oxamate and LDH. Using a high concentration of Bis would restrict the polymer chains due to high cross-linking density, making it difficult to observe swelling.

OxNPs were synthesized via precipitation polymerization in water and were purified by dialysis for 4 days to remove low molecular weight polymerization byproducts. Following dialysis, the yield of polymers was determined by weighing a lyophilized aliquot of NP solution (90% yield). Dynamic light scattering (DLS) was used to determine the hydrodynamic diameter of the particles and their polydispersity (Experimental Section). Because NIPAm polymers exhibit an LCST~32° C., particle size was measured at both 25° C. and 37° C. Below the LCST at 25° C., the hydrodynamic diameter of OxNPs was 403±7 nm. At 37° C., OxNP diameter decreased to 183±1 nm. Since these particles have intended applications under physiological conditions, 37° C. was chosen for all measurements and experimental conditions. Particle size was designed to be at or below 200 nm at body temperature to take advantage of the enhanced permeability and retention effect which promotes accumulation of nanoparticles in tumor tissues and to prevent encumbered circulation.

Quantification of LDH Uptake

Following OxNPs synthesis the next step was to study LDH uptake by OxNPs. The $K_m$ of oxamate for *Bacillus stearothermophillus* LDH is 0.6 mM. For LDH to serve as a cross-link, it must bind to two or more oxamate groups. This is realized under conditions where LDH is present as a homomeric tetramer with four discrete binding sites for oxamate groups. These conditions are realized in the presence of $NAD^+$ and fructose bisphosphate (FBP) which were present in all binding and uptake studies.

Figure 17:
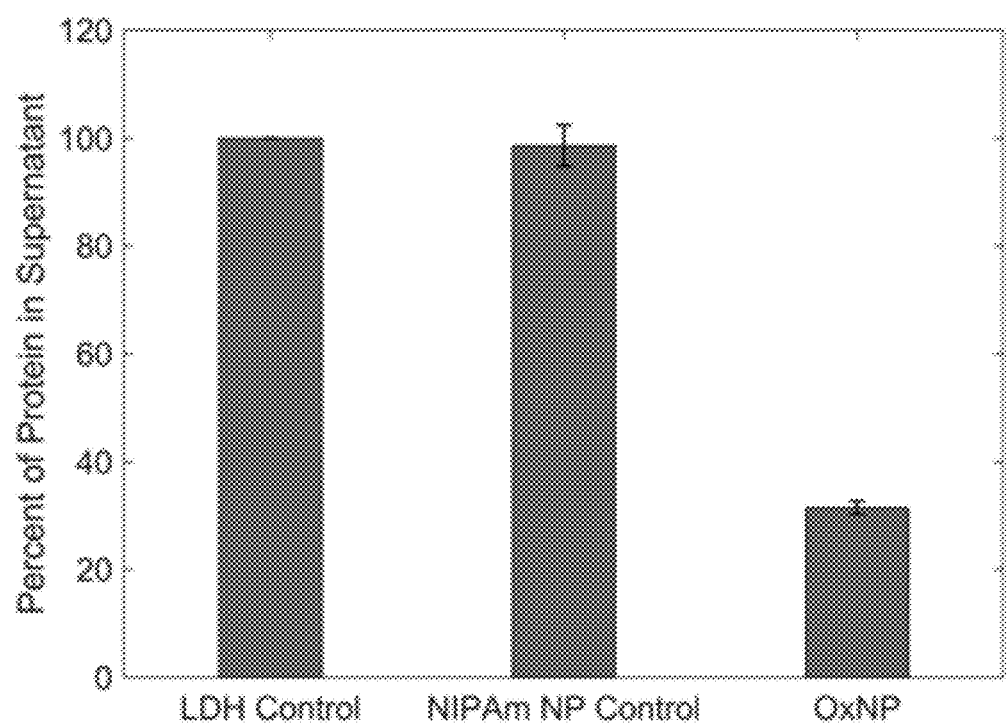
FIG. 17 shows a graph illustrating quantification of LDH uptake by NPs. Centrifugation was performed to pull down NP-LDH complexes leaving the unbound protein free in supernatant. Bars represent amount of LDH leftover in supernatant. LDH Control corresponds to the maximum amount of LDH added to solutions. NIPAm NP Control represents NIPAm NPs without oxamate inhibitor incubated with LDH. OxNP represent NIPAm NPs containing the oxamate inhibitor. The NIPAm NP Control showed no affinity for LDH while the OxNP demonstrated affinity for LDH.

OxNPs were incubated with LDH and its coenzymes FBP and $NAD^+$ at room temperature to allow LDH to diffuse into the solvent swollen OxNPs and bind to the polymer bound oxamate groups. After 30 min at room temperature, samples were heated to 37° C. for 10 min. Protein uptake was followed by centrifugation of OxNP-LDH complexes, which pelleted at the bottom, leaving unbound LDH in the supernatant. Protein concentration in the supernatant was determined using tryptophan fluorescence (Ex 280 nm, Em 342 nm) standardized against known concentrations of LDH. The results are summarized in FIG. 17. Control experiments with unfunctionalized (no oxamate ligands) NIPAm NPs (98 mol % NIPAm and 2 mol % Bis) were included for comparison. OxNPs (0.4 mg/mL) were calculated to bind 0.24 mg/mL of LDH in solution. Control NPs showed negligible LDH uptake. The wt:wt ratio of LDH to OxNPs was calculated to be 0.6 to 1.0. Using size exclusion multi-angle light scattering (SEC-MALS), OxNP molecular weight was determined to be $M_n$ of $2.276 \times 10^8$, $M_w$ of $2.863 \times 10^8$, with a PDI of 1.26. Using the known molecular weight of LDH (140 kDa for the tetramer) and OxNP ($M_n$ of $2.276 \times 10^8$) one calculates approximately 1000 proteins per OxNP. Despite this seemingly large number, less than 1% of the OxNP volume is taken up by LDH. This was derived after determining the density of OxNPs (0.01 g/mL assuming the OxNPs are spherical) and using an assumed density of 1.3 g/mL for LDH. The density calculated for OxNPs does not include the water hydrating the polymer.

Circular Dichroism (CD) Measurements

Figure 18:
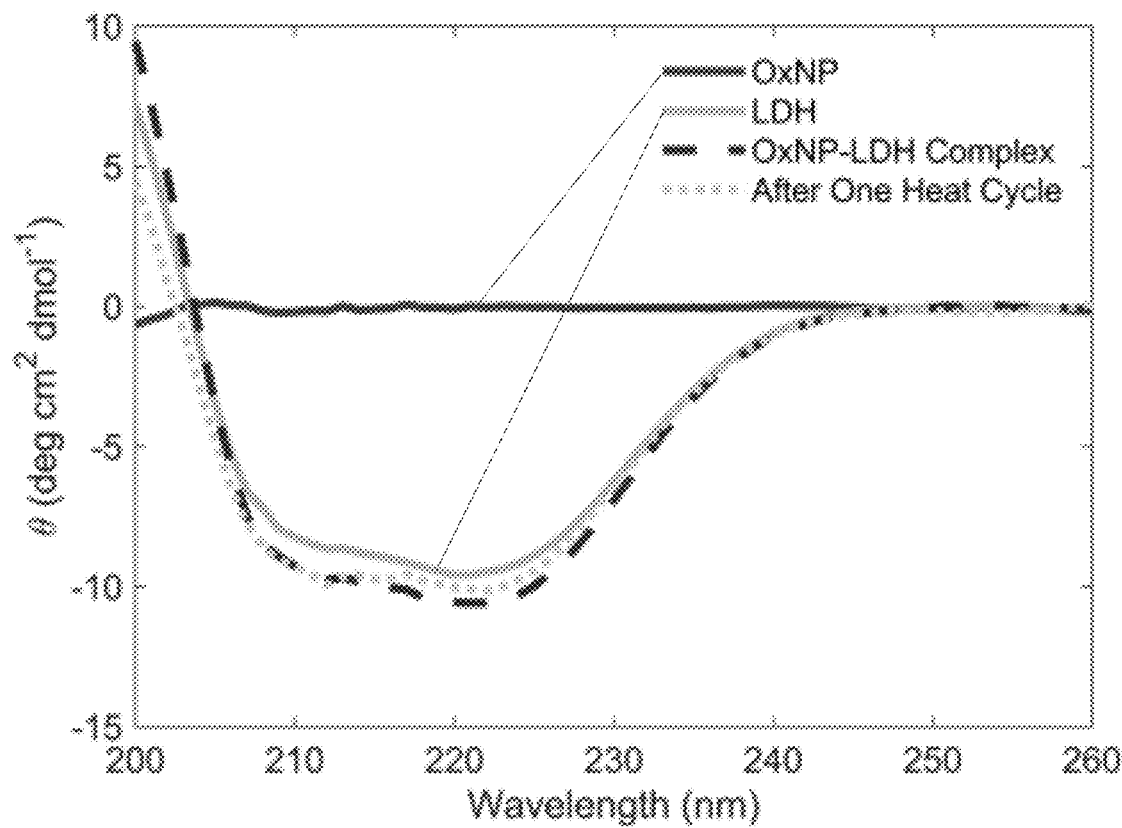
FIG. 18 shows a graph illustrating CD Measurements of OxNPs and LDH. CD was performed on OxNP alone and showed no signal. LDH was measured alone as a baseline. OxNP-LDH complexes showed no significant difference from the baseline LDH. After one heat cycle corresponds to measurements of OxNP-LDH complexes after being heated at 37° C. for 10 minutes followed by cooling and measurement. Each set of conditions demonstrated no denaturation occurring.
Figure 19:
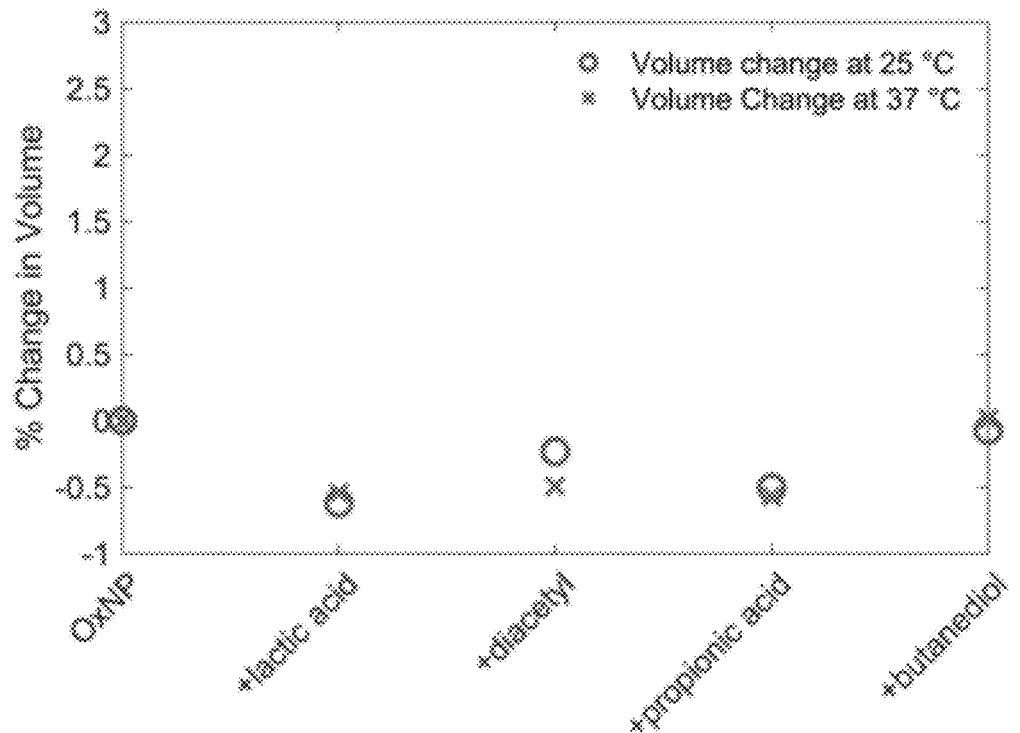
FIG. 19 shows a graph illustrating the change in volume of OxNP exposed to small molecules at 25° C. and 37° C. All small molecules had a concentration of 10 mM. Pyruvic acid and oxalic acid not shown.

Non-covalent complexation of LDH with OxNPs and subsequent thermal cycling of the copolymer-protein complex could subject the protein to structural deformation and/or denaturation. To evaluate this, CD spectroscopy was used to interrogate the OxNP-LDH complex. Samples containing OxNPs alone, LDH alone (both at room temperature and 37° C.), OxNP-LDH complexes prepared at room temperature, and OxNP-LDH complexes prepared at room temperature followed by heating to 37° C. and cooling to room temperature were evaluated. In all cases, the alpha helical motifs in LDH were maintained (FIG. 18). OxNPs do not disrupt the secondary structure of LDH. These results also indicate that the mechanical distortions from the polymer network's contraction at 37° C. and expansion at room temperature are insufficient to produce detectable distortions in the non-covalently bound protein.

Response of OxNP to Small Molecules

To establish that the OxNP-LDH complexes are metabolite (lactate) responsive, several controls with OxNPs were performed. DLS was used to monitor the change in size upon exposure of OxNPs to 10 mM solutions of lactic acid and several small molecules containing three or four carbons with either mono- or difunctional carboxylic acid and alcohol moieties at 25° C. and 37° C. It was discovered at 37° C., pyruvic acid and oxalic acid caused aggregation (not swelling) of OxNPs, a conclusion supported by the high polydispersity (0.23±0.2 for pyruvic acid and 0.096±0.02 for oxalic acid). Because these two molecules cause aggregation of OxNPs, they were not included in tests on OxNP-LDH complexes. The response of OxNPs to lactic acid, diacetyl, propionic acid, and 2,3-butanediol are shown in FIG. 18. None of the small molecules significantly affected the size of OxNPs at 25° C. or 37° C.

Response of OxNP-LDH Complexes to Small Molecules

A similar set of experiments was used to evaluate the response of the NP-protein complexes (OxNP-LDH complexes) to lactic acid and related small molecules. To establish a baseline for the OxNP-LDH complexes, DLS measurements were run in water at 25° C. and 37° C. At 25° C., the complexes had an average size of 308±3 nm and 180±1 nm at 37° C. One important observation is the change in size of OxNP at 25° C. when LDH is added, the resulting complex is about 100 nm smaller than OxNP by itself (403±7 nm). In contrast, NIPAm NPs do not experience a significant change in size when exposed to LDH at 25° C. (337±8 nm without LDH to 338±5 nm with LDH). The decrease in size of OxNP after exposure to LDH at 25° C. is consistent with the uptake of tetrameric LDH and cross-linking the polymer backbone by binding at least two polymer-bound oxamate moieties. It is reasonable that this shrinkage upon LDH cross-linking would be more apparent when performed in the solvent swollen state (25° C.).

Figure 20:
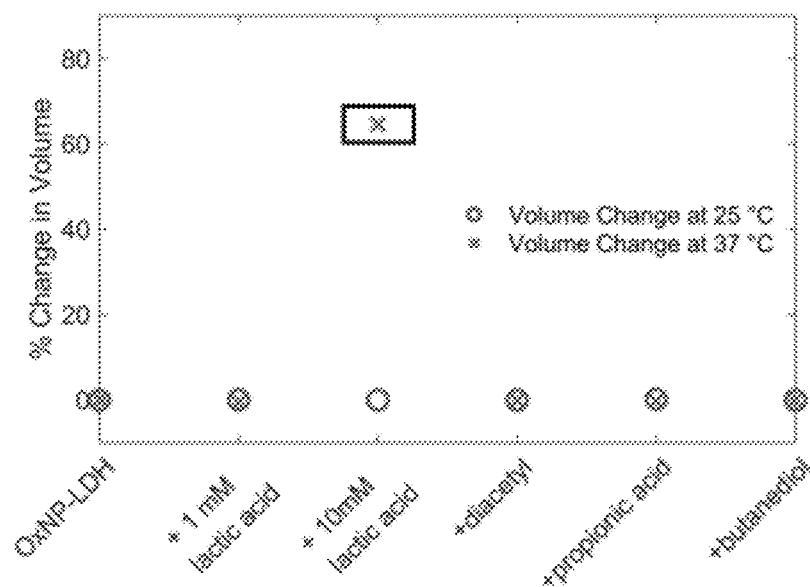
FIG. 20 shows a graph illustrating the change in volume of OxNP-LDH complexes exposed to small molecules at 25° C. and 37° C. Low lactic acid concentrations mirroring those found in healthy tissues (1 mM) do not cause a change in volume. High lactic acid concentrations (10 mM) cause a significant change in volume of OxNP-LDH complexes. The box highlights the data point correlated to a large change in volume at 37° C. Other small molecules (10 mM) elicited no effect on OxNP-LDH complex volume.

With the preceding benchmarks, the response of OxNP-LDH to small molecules was examined. The conditions were similar to the previous experiment but an additional trial using 1 mM of lactic acid was used to establish if OxNP-LDH complexes exhibit a concentration dependent response to lactic acid. The results, shown in FIG. 20, reveal there were no significant changes in volume of OxNP-LDH at 25° C. in the presence of any small molecules at 10 mM concentration.

At 37° C. the volume of OxNP-LDH complexes remained constant with one exception, lactic acid. OxNP-LDH samples treated with 10 mM lactic acid at 37° C. experienced a significant increase in volume. In contrast, 1 mM of lactic acid did not influence the volume of OxNP-LDH complexes. The increase in OxNP-LDH complex volume upon exposure to 10 mM lactic acid may arise from a combination of effects which include lactate displacement of the polymer bound oxamate moieties resulting in reduced cross-linking, electrostatic interactions, solvation, and possibly the catalytic activity of LDH. Importantly, 10 mM lactate was the only condition that induced a response.

Due to the sensitivity of NIPAm systems to a variety of external factors, it is important to consider alternative explanations. Although NIPAm is sensitive to changes in temperature, pH, and solvent ionic strength, the observed increase in size is not accounted for by these factors. However, it was considered that pH may partially or indirectly contribute to the observed swelling. Kratz et al. demonstrated a size increase of NIPAm NPs containing low loadings (1.25 mol % and 12.5 mol %) of acrylic acid (AAc) at low pH above their LCST. Because the oxamate derivative incorporated into the polymer also has a carboxylic moiety, comparisons may be drawn between the 1.25 mol % loaded AAc NIPAm polymer and the system of the present invention (OxNP). Kratz attributed this observation to an expected collapse (desolvation) above LCST, but the collapsed NPs were prone to form somewhat uniform aggregates at low pH. This behavior was attributed to weak interparticle interactions. They also observed that this was completely reversible.

The pH of OxNP solutions drops significantly upon addition of lactic acid. If the observed swelling of OxNP-LDH complexes in 10 mM lactic acid was solely pH dependent, one would have expected OxNPs to have exhibited the same response when exposed to lactic acid at 37° C. This, however, was not observed. Furthermore, at lactic acid concentrations similar to those found in healthy tissues in the body (1 mM), there is no response of OxNP-LDH complexes. Once lactic acid concentrations exceed the normal range, only NP-protein complexes (OxNP-LDH) responded. Therefore, the increase in size may be due to a reduction in cross-linking brought about by competitive displacement of the polymer bound oxamate moiety by lactic acid.

One main hypothesis is that lactic acid competitively displaces the polymer bound oxamate moiety, decreasing the cross-linking of the OxNP. However, due to the complexity of this system, it is not unreasonable to think that other factors might also contribute. For example, under 10 mM lactate conditions there could be "open" active binding sites on the homomeric tetramer LDH. The generation of pyruvic acid within the OxNP could potentially contribute to swelling of particles since the $K_d$ of pyruvate is similar to that of oxamate, this could displace more oxamate moieties and further increase swelling. Although this potential exists, this is not likely the most significant reason for swelling. Experiments involving OxNP and OxNP-LDH complexes with pyruvic acid led to irreversible aggregation of particles, unlike what was observed with lactic acid. This suggests there is something specific about lactic acid that does not lead to aggregation of particles, but instead leads to swelling.

Scanning Electron Microscopy Imaging of NPs

Figure 8A:
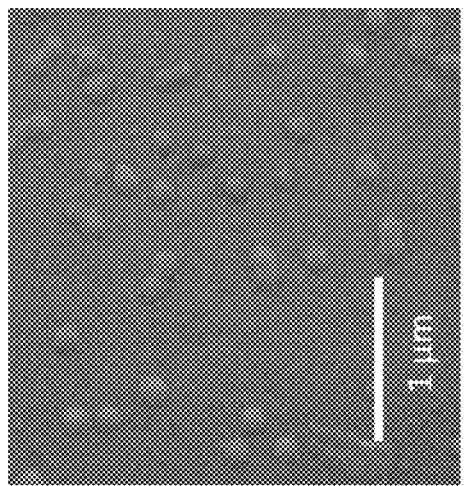
FIG. 8A shows a SEM image of inhibitor containing NPs.
Figure 11A:
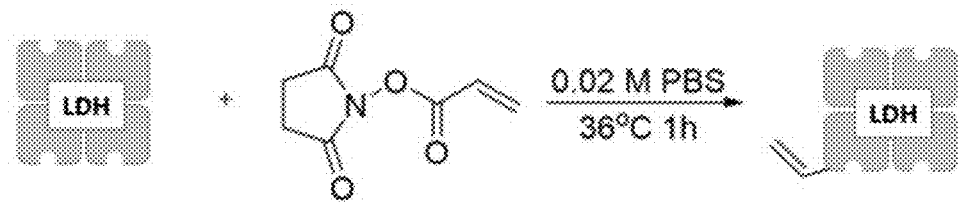
FIG. 11A shows a scheme describing the functionalization of the LDH with NSA to provide the vinyl group for LDH incorporation.
Figure 11B:
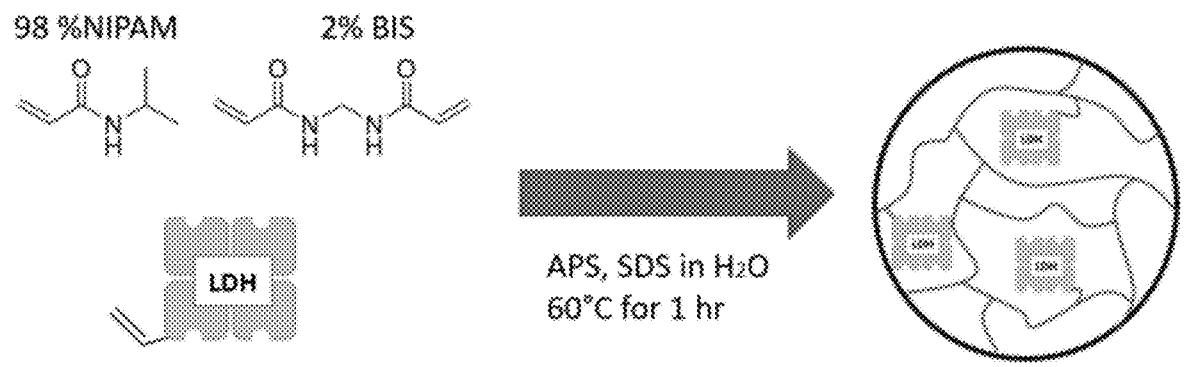
FIG. 11B shows a scheme describing the recipes for NP synthesis.
Figure 11C:
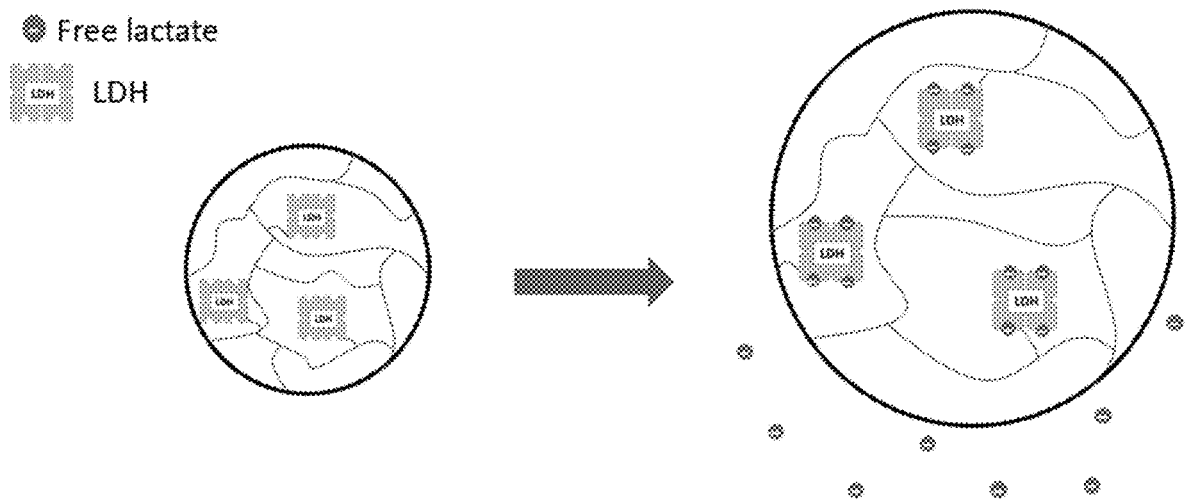
FIG. 11C shows a scheme explaining the mechanism in which the swelling occurs. The binding of the free lactate with negative charge causes the ionic swelling of the particle.
Figure 12A:
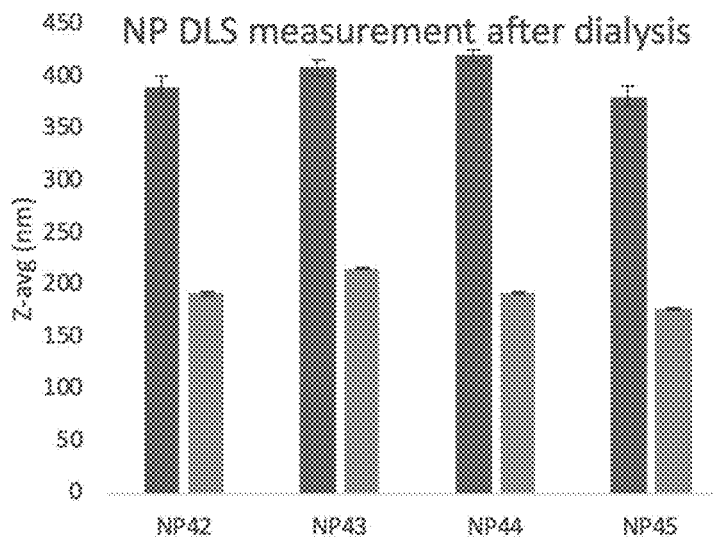
FIG. 12A shows a graph of dynamic light scattering (DLS) measurements illustrating thermal responsive behavior of NIPAM-LDH hybrid nanoparticles. The left bar for each particle is at 25° C. and the right bar for each particle is at 37° C.
Figure 12B:
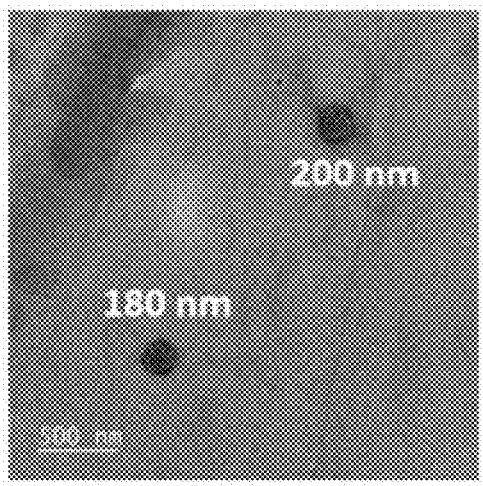
FIG. 12B shows a TEM image showing nanoparticles with comparable size to the DLS measurements.
Figure 12C:
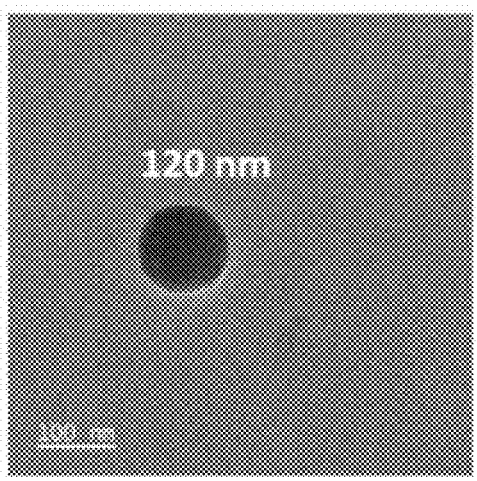
FIG. 12C shows a TEM image showing nanoparticles with comparable size to the DLS measurements.
Figure 13:
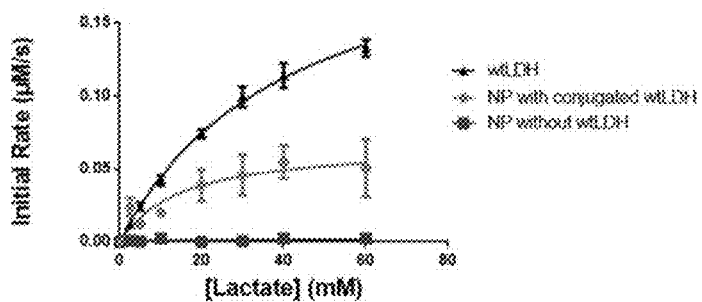
FIG. 13 shows a graph and a table illustrating enzyme kinetics of wtLDH within a nanoparticle. Conjugated LDH is active within nanoparticles, indicating structural integrity of protein.
Figure 14:
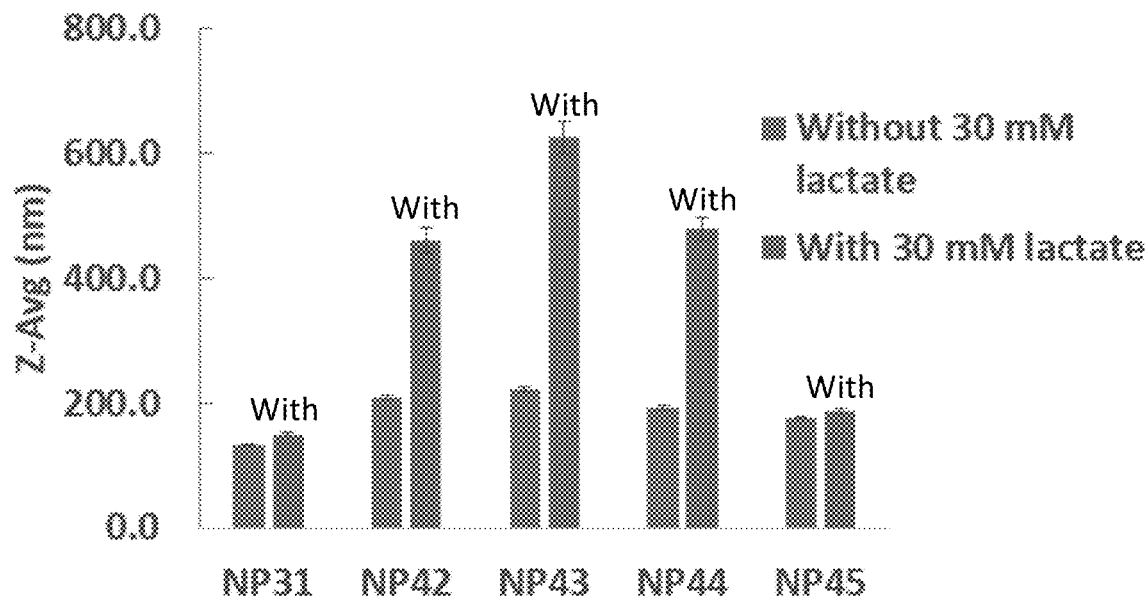
FIG. 14 shows a graph illustrating swelling characteristics of NPs at physiologically-relevant metabolite concentrations of lactate. NPs containing different LDH mutants swell to different degrees when lactate is present. The left bar for each particle is without 30 mM lactate and the right bar for each particle is with 30 mM lactate.
Figure 15:
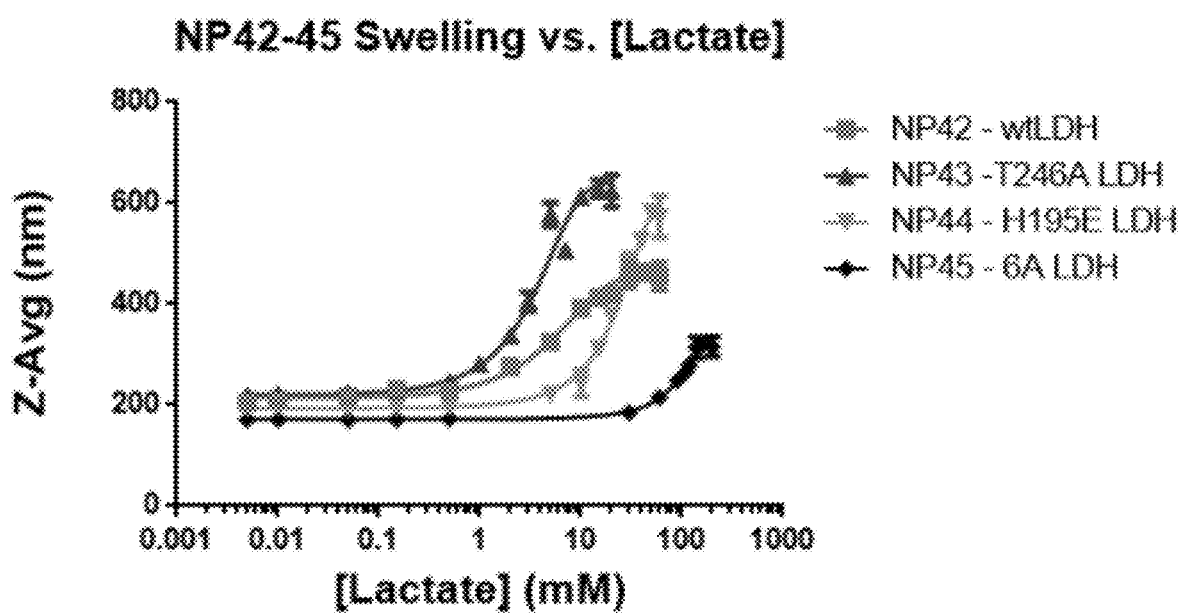
FIG. 15 shows a swelling profile graph. NP size vs. [lactate] of NPs synthesized with different mutant LDH exhibit different responses to lactate concentrations.

Scanning electron microscopy (SEM) was performed on OxNPs and lactic acid exposed OxNP-LDH complexes (FIGS. 8A-8C) to observe the size change of OxNP-LDH complexes in the presence of 10 mM lactic acid. Samples were prepared by drop-casting a solution of OxNP in water onto glass slides then heated at 150° C. until dry. To establish a point of reference, SEM images were taken of OxNPs (FIG. 8A). The size of OxNPs in FIGS. 8A and 8B (~160 nm) are roughly the same as those measured by DLS at 37° C. (183±1 nm). These images are consistent with the experimental results obtained by DLS for lactic acid responsiveness.

Cryo-Transmission Electron Microscope Images

Figure 21A:
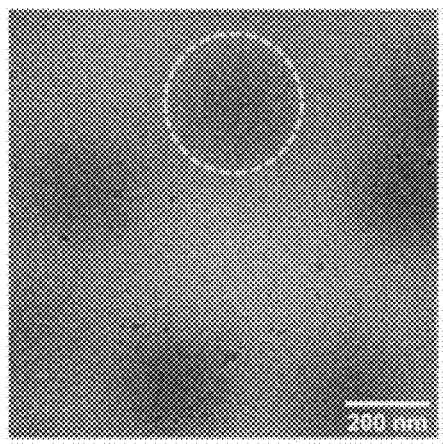
FIGS. 21A-D show cryoTEM images of OxNPs and OxNP-LDH complexes.
Figure 21B:
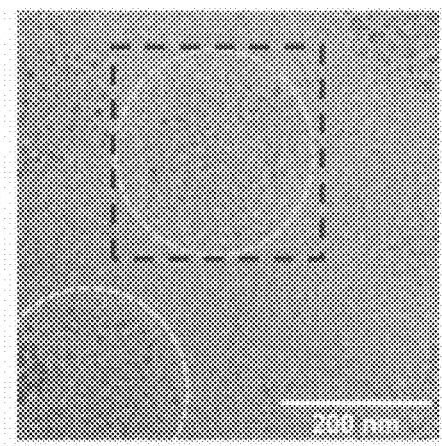
Figure 21C:
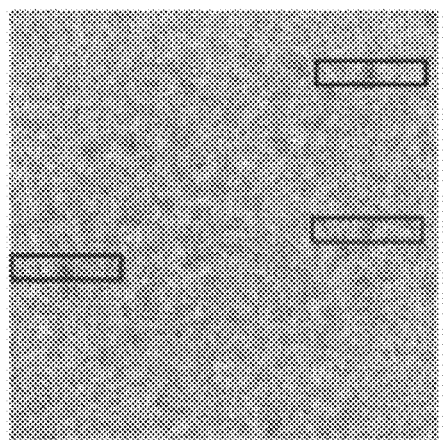
Figure 21D:
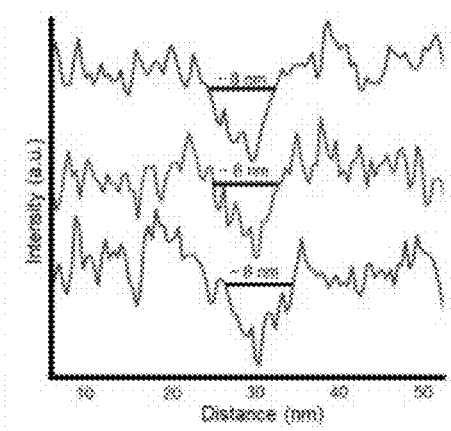

To further characterize OxNP-LDH complexes, cryo-transmission electron microscopy (cryoTEM) was employed, which enables the native state of the OxNPs to be imaged at high resolution (FIGS. 21A-21D). Due to the 100-fold difference in density between OxNPs (0.01 g/mL) and LDH (1.3 g/mL), the contrast will be dominated by the LDH particles. At high defocus values (~10-20 microns), the OxNP-LDH complexes are easily identifiable and appear as homogeneous spheres with a 200 nm diameter (FIG. 21A, highlighted with the dashed blue circles). This is consistent with the DLS measurements. At lower defocus values (~0.5-1 micron) the OxNP-LDH complexes display extremely low contrast (FIG. 21B, highlighted by the dashed blue circles), but the resolution is sufficient to identify individual LDH particles (FIG. 21C). Due to the superposition of the LDH particles it is only possible to measure their individual diameter (~8 nm) close to the edge of the structures, however, this is consistent with their previously measured $R_H$ values (~4.3 nm).

If LDH bound selectively to the surface, there would be a distinct and visible ring around the OxNPs; consequently, it was inferred that LDH distributed through the 3D volume of the OxNPs. This is consistent with the observation that OxNPs contract when exposed to LDH by 100 nm, and OxNP-LDH complexes swell when exposed to lactate. If LDH were confined to the surface of the OxNPs, cross-linking and subsequent swelling would be minimized.

In summary, a polymerizable oxamate LDH inhibitor 6 was synthesized and incorporated into lightly cross-linked NIPAm NPs, producing OxNPs. LDH was efficiently taken up into OxNPs in the solvent-swollen state through incubation and non-covalent binding to the polymer bound oxamate moieties in the polymer backbone. Protein loading was estimated to be 0.6 mg LDH/1 mg OxNP. CD was used to demonstrate that OxNPs do not lead to distortion or denaturation of LDH's secondary structure after being exposed to OxNPs below and above LCST as well as after one full heating cycle, which is important for cross-linking. OxNP-LDH complexes showed a large swelling response in the presence of high lactic acid concentrations (10 mM), but none at low lactic acid concentrations (1 mM). OxNP-LDH complexes exposed to lactic acid below LCST behave normally and remain the same size as without lactic acid. Above the LCST, lactic acid treated OxNP-LDH complexes swell almost double their size at room temperature. SEM was also used to visualize OxNP-LDH complex's response to lactic acid. Through TEM, OxNP-LDH complexes were imaged to further validate uptake. A metabolite-responsive system has been developed. OxNP-LDH complexes swell in the presence of high lactic acid concentrations that mirror those found in tumors. The influence of temperature and lactic on particle swelling only influences OxNPs when they are complexed with LDH. This supports the hypothesis that LDH acts as a cross-linker within the polymer and is displaced in the presence of lactic acid. The system of the present invention provides a platform for metabolite responsive NPs.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A nanoparticle for drug delivery, configured to release an encapsulated drug in response to a lactate metabolite, the nanoparticle comprising:
   a. a polymer hydrogel;
   b. the drug, encapsulated within the polymer hydrogel;
   c. a protein encapsulated within the polymer hydrogel having a binding site for the lactate metabolite, wherein the protein is lactate dehydrogenase (LDH) or a mutant or derivative thereof;
   d. an inhibitor with affinity for the binding site of the protein, the inhibitor covalently attached to the polymer hydrogel and bound within the binding site of the protein;
   wherein the inhibitor is configured to be displaced from the binding site of the protein when the nanoparticle is exposed to a concentration of the lactate metabolite greater than a normal concentration of the lactate metabolite, and
   wherein displacement of the inhibitor is configured to cause release of the drug from the nanoparticle.

2. A metabolite responsive nanoparticle for targeted drug delivery to treat a condition associated with a lactate metabolite, comprising:
   a. a N-isopropylacrylamide (NIPAm) polymer hydrogel;
   b. a hydrophobic chemotherapeutic anti-cancer drug encapsulated within the polymer hydrogel;
   c. a protein encapsulated within the polymer hydrogel, having a binding site for the lactate metabolite, wherein the protein is lactate dehydrogenase (LDH) or a mutant or derivative thereof;
   wherein the nanoparticle is configured to release the drug when the nanoparticle is exposed to the lactate metabolite.

3. The nanoparticle of claim 2, additionally comprising an oxamate inhibitor with affinity for the binding site of the protein, the oxamate inhibitor covalently attached to the polymer hydrogel and bound within the binding site of the protein;
   wherein the oxamate inhibitor is configured to be displaced from the binding site of the protein when the nanoparticle is exposed to a concentration of the lactate metabolite greater than a normal concentration of the lactate metabolite, and
   wherein displacement of the oxamate inhibitor is configured to cause release of the drug from the nanoparticle.

* * * * *